(12) United States Patent
Jorgensen

(10) Patent No.: US 8,492,415 B2
(45) Date of Patent: Jul. 23, 2013

(54) AZOLES AND RELATED DERIVATIVES AS NON-NUCLEOSIDE REVERSE TRANSCRIPTASE INHIBITORS (NNRTIS) IN ANTIVIRAL THERAPY (HIV)

(75) Inventor: William L. Jorgensen, Deep River, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 12/452,151

(22) PCT Filed: Jul. 2, 2008

(86) PCT No.: PCT/US2008/008214
§ 371 (c)(1),
(2), (4) Date: Feb. 4, 2010

(87) PCT Pub. No.: WO2009/005811
PCT Pub. Date: Jan. 8, 2009

(65) Prior Publication Data
US 2010/0168190 A1     Jul. 1, 2010

Related U.S. Application Data

(60) Provisional application No. 60/958,392, filed on Jul. 3, 2007.

(51) Int. Cl.
| *A61K 31/41* | (2006.01) |
| *A61K 31/422* | (2006.01) |
| *A61K 31/4245* | (2006.01) |
| *A61K 31/426* | (2006.01) |
| *C07D 413/12* | (2006.01) |
| *C07D 271/113* | (2006.01) |
| *C07D 277/20* | (2006.01) |
| *C07D 285/135* | (2006.01) |

(52) U.S. Cl.
USPC ........... 514/363; 514/377; 514/364; 514/370; 548/234; 548/143; 548/190; 548/138

(58) Field of Classification Search
USPC .................. 514/363, 364, 370, 377; 548/138, 548/143, 190, 234
See application file for complete search history.

(56) References Cited

U.S. PATENT DOCUMENTS 7,208,509 B2     4/2007   Dunn et al.
2003/0220315 A1  11/2003  Cushman et al.

FOREIGN PATENT DOCUMENTS

WO     WO 97/24340 A1  *  7/1997

OTHER PUBLICATIONS

Vippagunta et al., Crystalline solids, 2001, Advanced Drug Delivery Reviews, 48, pp. 3 and 18.*

Zeevaart et al., Optimization of Azoles as Anti-Human Immunodeficiency Virus Agents Guided by Free-Energy Calculations, 2008, J. Am. Chem. Soc., 130, 9492-9499.*
Robert Robinson, A New Synthesis of Oxazole Derivatives, 1909, Journal of the Chemical Society, Transactions, 95, 2167-2174.*
2006 AIDS Epidemic Update: UNAIDS: Geneva, 2006.
Kohlstaedt, L. A.; Wang, J.; Friedman, J. M.; Rice, P. A.; Steitz, T. A. Science 1992, 256, 1783-1790.
Smerdon, S. J.; Jager, J.; Wang, J.; Kohlstaedt, L. A.; Chirino, A. J.; Friedman, J. M.; Rice, P. A.; Steitz, T. A. Proc. Natl. Acad. Sci. U.S.A. 1994, 91, 3911-3915.
De Clercq, E. J. Med. Chem. 2005, 48,1297-313.
Jorgensen, W. L.; Ruiz-Caro, J.; Tirado-Rives, J.; Basavapathruni, A.; Anderson, K. S.; Hamilton, A. D. Bioorg. Med. Chem. Lett. 2006, 16, 663-667.
Ruiz-Caro, J.; Basavapathruni, A.; Kim, J. T.; Wang, L.; Bailey, C. M.; Anderson, K. S.; Hamilton, A. D.; Jorgensen, W. L. Bioorg. Med. Chem. Lett. 2006. 16, 668-671.
Thakur, V. V.; Kim, J. T.; Hamilton, A. D.; Bailey, C. M.; Domaoal, R. A.; Wang, L.; Anderson, K. S.; Jorgensen, W. L. Bioorg. Med. Chem. Lett. 2006, 16, 5664-5667.
Kim, J. T.; Hamilton, A. D.; Bailey, C. M.; Domaoal, R. A.; Wang, L.; Anderson, K. S.; Jorgensen, W. L. J. Am. Chem. Soc. 2006, 128,15372-15373.
Blake, J. F.; Laird, E. R. Ann. Rep. Med. Chem. 2003, 38, 305-314.
Leach, A. R.; Shoichet, B. K.; Peishori, C. E. J. Med. Chem. 2006, 49, 5851-5855.
11) Barreiro, G.; Guimaraes, C. R. W.; Tubert-Brohman, I.; Tirado-Rives, J.; Jorgensen, W. L., J. Chem. Info. Model., 2007,47,2416-2428.
Ren, J.; Esnouf, R. M.; Hopkins, A. L.; Warren, J.; Balzarini, J.; Stuart, D. I.; Stammers, D. K. Crystal structures of HIV-1 reverse transcriptase in complex with carboxanilide derivatives. Biochemistry 1998, 37, 14394-14403.
Friesner, R. A.; Banks, J. L.; Murphy, R. B.; Halgren, T. A.; Klicic, J. J.; Mainz, D. T.; Repasky, M. P.; Knoll, E. H.; Shelley, M.; Perry, J. K.; Shaw, D. E.; Francis, P.; Shenkin, P. S. J. Med. Chem. 2004, 47, 1739-1749.
Jorgensen, W. L.; Maxwell, D. S.; Tirado-Rives, J. J. Am. Chem. Soc. 1996, 118, 11225-11236.
Jorgensen, W. L.; Tirado-Rives, J. Proc. Nat. Acad. Sci USA 2005, 102, 6665-6670.
Still, W. C.; Tempczyk, A.; Hawley, R. C.; Hendrickson, T. J. Am. Chem. Soc. 1990, 112, 6127-6129.
Jorgensen, W. L.; Ulmschneider, J. P.; Tirado-Rives, J. J. Phys. Chem. B 2004, 108, 16264-16270.
MacroModel, version 9.0, Schrodinger LLC, New York, NY, 2005.
Lin, T. S.; Luo, M. Z.; Liu, M. C.; Pai, S. B.; Dutschman, G. E.; Cheng, Y. C. Biochem. Pharmacol. 1994, 47, 171-174.
Ray, A. S.; Yang, Z.; Chu, C. K.; Anderson, K. S. Antimicrob. Agents Chemother. 2002, 46, 887-891.
Muraglia, E.; Kinzel, O. D.; Laufer, R.; Miller, M. D.; Moyer, G.; Munshi, V.; Orvieto, F.; Palumbi, M. C.; Pescatore, G.; Rowley, M.; Williams, P. D.; Summa, V. Bioorg. Med. Chem. Lett. 2006, 16, 2748-2752.
Wang, Z.; Wu, B.; Kuhen, K. L.; Bursulaya, B.; Nguyen, T. N.; Nguyen, D. G.; He, Y. Bioorg. Med. Chem. Lett. 2006, 16, 4174-4177.

(Continued)

*Primary Examiner* — Kristin Bianchi
(74) *Attorney, Agent, or Firm* — Henry D. Coleman; R. Neil Sudol

(57) ABSTRACT

The present invention relates to novel heterocyclic compounds, including oxadiazole compounds, pharmaceutical compositions and their use in the inhibition of reverse transcriptase and the treatment of HIV (1 and 2) infections, AIDS and ARC and other viral infections.

68 Claims, 17 Drawing Sheets

OTHER PUBLICATIONS

De La Rosa, M.; Kim, H. W.; Gunic, E.; Jenket, C.; Boyle, U.; Koh, Y.-H.; Korboukh, I.; Allan, M.; Zhang, W.; Chen, H.; Xu, W.; Nilar, S.; Yao, N.; Hamatake, R.; Lang, S. A.; Hong, Z.; Zhang, Z. & Girardet, J.-L. Bioorg. Med. Chem. Lett. 2006, 16, 4444-4449.

Tirado-Rives, J.; Jorgensen, W. L. J. Med. Chem. 2006, 49, 5880-5884.

Hann, M. M.; Leach, A. R.; Harper, G. J. Chem. Inf. Comput. Sci. 2001, 41, 856-864.

Rizzo, R. C.; Udier-Blagovic, M.; Wang, D. P.; Watkins, E. K.; Kroeger Smith, M. B.; Smith, Jr., R. H.; Tirado-Rives, J.; Jorgensen, W. L. J. Med. Chem. 2002, 45, 2970-2987.

Blagovic, M. U.; Tirado-Rives, J.; Jorgensen, W. L. J. Am. Chem. Soc. 2003, 125, 6016-6017.

Das, K.; Clark, A. D., Jr.; Lewi, P. J.; Heeres, J.; de Jonge, M. R.; Koymans, L. M. H.; Vinkers, H. M.; Daeyaert, F.; Ludovici, D. W.; Kukla, M. J.; De Corte, B.; Kavash, R. W.; Ho, C. Y.; Ye, H.; Lichtenstein, M. A.; Andries, K.; Pauwels, R.; de Bethune, M.-P.; Boyer, P. L.; Clark, P.; Hughes, S. H.; Janssen, P. A. J.; Arnold, E. J. Med. Chem. 2004, 47, 2550-2560.

Ludovici, D. W.; De Corte, B. L.; Kukla, M. J.; Ye, H.; Ho, C. Y.; Lichtenstein, M. A.; Kavash, R. W.; Andries, K.; de Bethune, M.-P.; Azijn, H.; Pauwels, R.; Lewi, P. J.; Heeres, J.; Koymans, L. M. H.; de Jonge, M. R.; Van Aken, K. J. A.; Daeyaert, F. F. D.; Das, K.; Arnold, E.; Janssen, P. A. J. Moorg. Med. Chem. Lett. 2001, 11, 2235-2239.

Heeres, J.; de Jonge, M. R.; Koymans, L. M. H.; Daeyaert, F. F. D.; Vinkers, M.; Van Aken Koen, J. A.; Arnold, E.; Das, K.; Kilonda, A.; Hoornaert, G. J.; Compernolle, F.; Cegla, M.; Azzam, R. A.; Andries, K.; de Bethune, M.-P.; Azijn, H.; Pauwels, R.; Lewi, P. J.; Janssen, P. A J J. Med. Chem. 2005, 48,1910-8.

QikProp, v 3.0; Schrodinger LLC: New York, 2006. QikProp is called as a subroutine by BOMB for each generated structure.

Himmel, D. M.; Das, K.; Clark, A. D., Jr.; Hughes, S. H.; Benjahad, A.; Oumouch, S.; Guillemont, J.; Coupa, S.; Poncelet, A.; Csoka, I.; Meyer, C.; Andries, K.; Nguyen, C. H.; Grierson D. S.; Arnold E. J. Med. Chem. 2005, 48, 7582-91.

Tsuzuki, S.; Houjou, H.; Nagawa, Y.; Hiratani, K. J. Chem. Soc. Perkin Trans. 2 2002, 1271-1273.

Jorgensen, W. L.; Tirado-Rives, J. J Comput. Chem. 2005, 26, 1689-1700.

Alanine, A.; Anselm, L.; Steward, L.; Thomi, S.; Vifian, W.; Groaning, M. D. Bioorg. Med. Chem. Lett. 2004,14, 817-821.

Van Dort, M.; Neubig, R.; Counsell, R. E. J. Med. Chem. 1987, 30, 1241-1244.

Zinner, G.; Heitmann, M. Arch. Pharm. 1981, 314,193-196.

Barreca, M. L.; De Luca, L.; Iraci, N.; Rao, A.; Ferro, S.; Maga, G.; Chimirri, A. J. Chem. Inf. Model. 2007,47,557-562.

\* cited by examiner

FIGURE 1
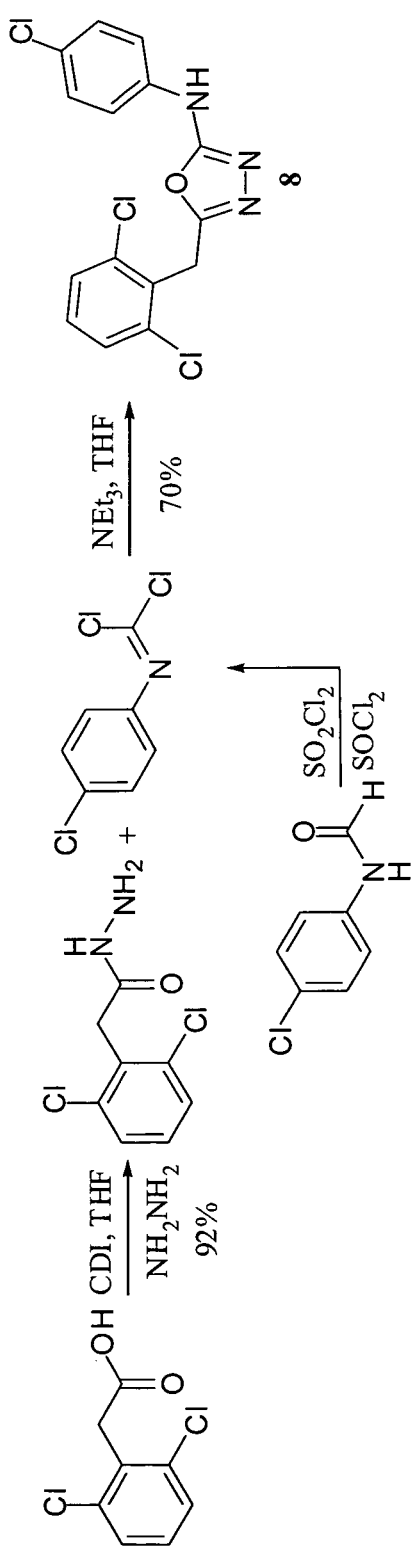
Scheme 1  Synthesis of Oxadiazole Compounds
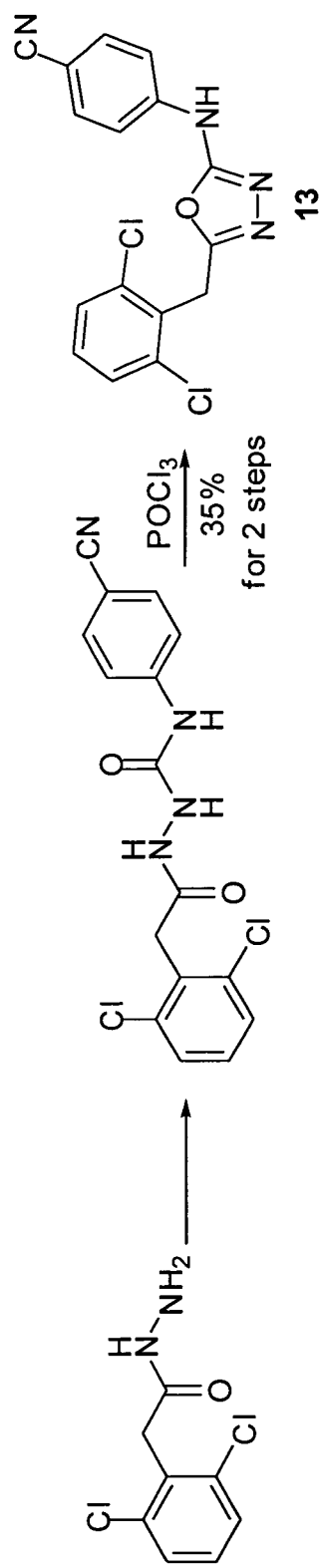
Scheme 2  Alternative Synthesis of Oxadiazole Compounds

FIGURE 2
Scheme 3 Synthesis of 1,3,4-oxadiazole-2,5-diamines
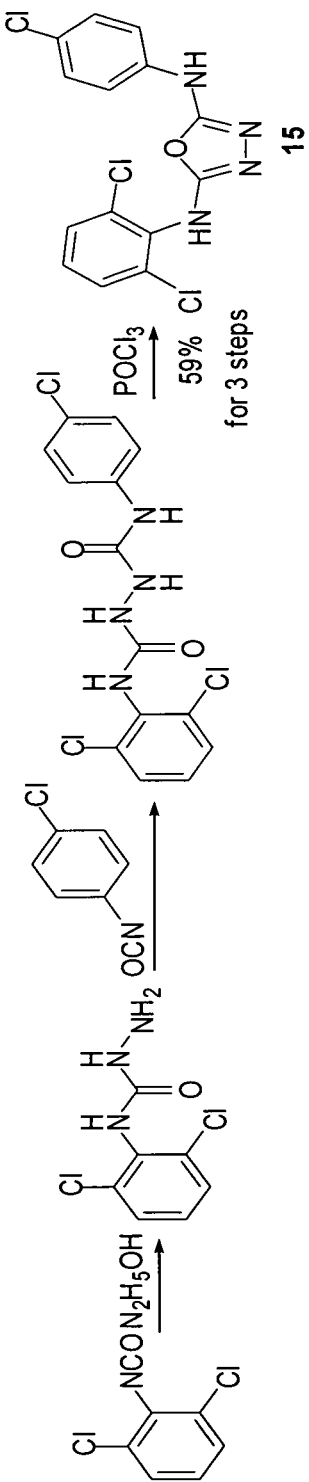
Scheme 4 Synthesis of 2,5-oxazole derivatives
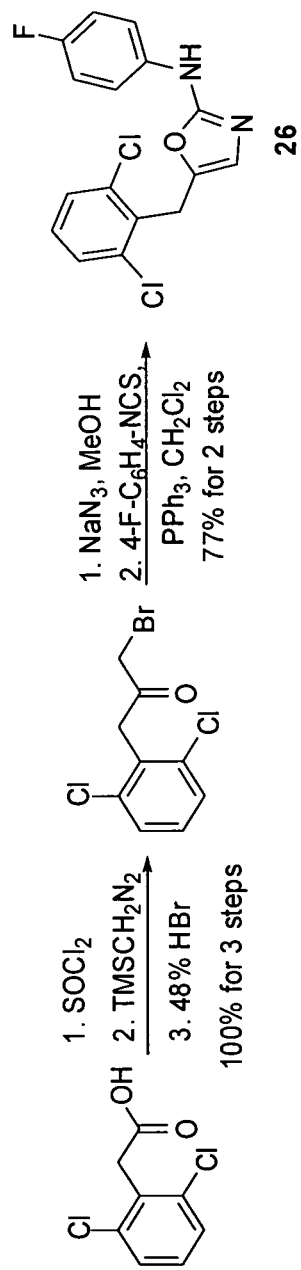

Figure 3

Table 1 Oxadiazoles: Anti-HIV-1 Activity (EC$_{50}$) and Cytotoxicity (CC$_{50}$) in µM

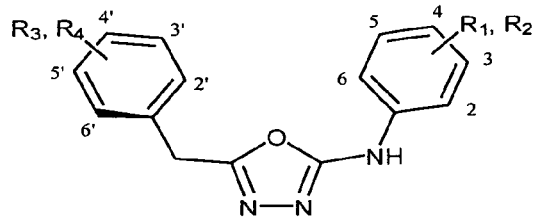

| Compd | R$_1$ | R$_2$ | R$_3$ | R$_4$ | EC$_{50}$[a] | CC$_{50}$[b] |
|---|---|---|---|---|---|---|
| 1 | 4-CH$_3$ | H | 3'-OCH$_3$ | 4'-OCH$_3$ | NA | 61 |
| 2 | H | H | H | H | NA | >100 |
| 3 | 4-Cl | H | H | H | NA | 31 |
| 4 | 4-Cl | H | 4'-Cl | H | NA | >100 |
| 5 | 4-Cl | H | 5'-Cl | H | >10 | 32 |
| 6 | 2-Cl | H | 2'-Cl | 6'-Cl | NA | >100 |
| 7 | 3-Cl | H | 2'-Cl | 6'-Cl | 4.3 | 71 |
| 8 | 4-Cl | H | 2'-Cl | 6'-Cl | 0.82 | 20 |
| 9 | 4-Cl | 2-Cl | 2'-Cl | 6'-Cl | 2.4 | 45 |
| 10 | 4-Cl | 3-Cl | 2'-Cl | 6'-Cl | 0.31 | >100 |
| 11 | 4-Cl | 3-CH$_3$ | 2'-Cl | 6'-Cl | 1.3 | >100 |
| 12 | 4-CH$_2$OCH$_3$ | H | 2'-Cl | 6'-Cl | 4.3 | 100 |
| 13 | 4-CN | H | 2'-Cl | 6'-Cl | 0.13 | 40 |
| 14 | 4-CN | H | 2'-F | 6'-F | 0.23 | 90 |
| d4T | | | | | 1.4 | >100 |
| nevirapine | | | | | 0.11 | >10 |
| efavirenz | | | | | 0.002 | >0.1 |

[a] For 50% protection in MT-2 cells; antiviral curves used triplicate samples at each concentration. NA for EC$_{50}$ > CC$_{50}$. [b] For 50% inhibition of MT-2 cell growth; toxicity curves also used triplicate samples.

FIGURE 4

Table 2 Benzylic Analogs: Anti-HIV-1 Activity (EC$_{50}$) and Cytotoxicity (CC$_{50}$) in µM.

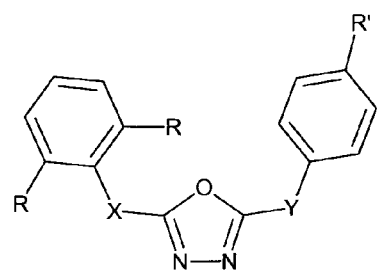

| Compd | R | R' | X | Y | EC$_{50}$[a] | CC$_{50}$[a] |
|---|---|---|---|---|---|---|
| 8 | Cl | Cl | CH$_2$ | NH | 0.82 | 20 |
| 15 | Cl | Cl | NH | NH | >100 | >100 |
| 16 | Cl | Cl | CH$_2$ | CH$_2$ | 18 | 43 |
| 13 | Cl | CN | CH$_2$ | NH | 0.13 | 40 |
| 17 | Cl | CN | NH | NH | 9.8 | >100 |
| 18 | Cl | CN | NCH$_3$ | NH | 0.27 | >100 |
| 19[b] | Cl | CN | CHCH$_3$ | NH | 1.20 | 54 |
| 20[b] | F | CN | CHCH$_3$ | NH | 0.13 | 8.5 |

[a] For 50% protection in MT-2 cells; antiviral curves used triplicate samples at each concentration. NA for EC$_{50}$ > CC$_{50}$. For 50% inhibition of MT-2 cell growth; toxicity curves also used triplicate samples. [b] Racemate.

FIGURE 5

Table 3 Heterocycle Analogs: Anti-HIV-1 Activity (EC$_{50}$) and Cytotoxicity (CC$_{50}$) in μM

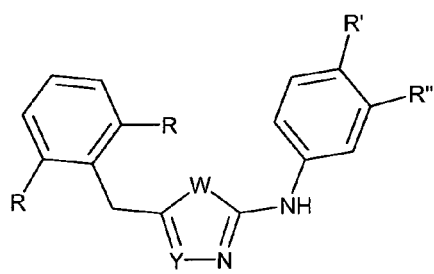

| Compd | R | R' | R" | W | Y | EC$_{50}$[a] | CC$_{50}$[a] |
|---|---|---|---|---|---|---|---|
| 21 | Cl | Cl | H | S | N | NA | >100 |
| 22 | Cl | Cl | H | S | CH | 3.1 | 29 |
| 23 | Cl | Cl | Cl | S | CH | 1.4 | 9.8 |
| 24 | Cl | CN | H | S | CH | 0.43 | >100 |
| 25 | Cl | Et | H | O | CH | 2.8 | >100 |
| 26 | Cl | F | H | O | CH | 0.43 | 12 |
| 27 | Cl | Cl | H | O | CH | 0.11 | 2.8 |
| 28 | Cl | CN | H | O | CH | 0.022 | 2.1 |
| 29 | F | CN | H | O | CH | 0.013 | 7.4 |

[a] For 50% protection in MT-2 cells; antiviral curves used triplicate samples at each concentration. NA for EC$_{50}$ > CC$_{50}$. [b] For 50% inhibition of MT-2 cell growth; toxicity curves also used triplicate samples; ND = not determined.

FIGURE 6

Table 4 Activity ($EC_{50}$) and Cytotoxicity ($CC_{50}$) in μM for Wild-Type and Variant Strains of HIV-1[a]

| Compd | WT $EC_{50}$ | $CC_{50}$ | Y181C $EC_{50}$ | $CC_{50}$ | K103N/Y181C $EC_{50}$ | $CC_{50}$ |
|---|---|---|---|---|---|---|
| 13 | 0.13 | 40 | 21 | 72 | 24 | >100 |
| 27 | 0.11 | 2.8 | NA | 6 | NA | 15 |
| 28 | 0.022 | 2.1 | NA | 4 | NA | 5 |
| 29 | 0.013 | 7.4 | NA | 8 | ND | ND |
| d4T | 1.4 | >100 | 0.68 | >100 | 0.28 | >100 |
| efavirenz | 0.002 | >0.1 | 0.013 | >0.1 | 0.050 | >0.1 |
| TMC125 | 0.001 | >0.1 | 0.014 | ND | 0.005 | ND |

[a] For 50% protection in MT-2 cells; antiviral curves used triplicate samples at each concentration. NA for $EC_{50} > CC_{50}$. [b] For 50% inhibition of MT-2 cell growth; toxicity curves also used triplicate samples; ND = not determined.

FIGURE 7

Table 5 Further Oxadiazole Analogs: Anti-HIV-1 (EC$_{50}$) and Cytotoxicity (CC$_{50}$) in µM

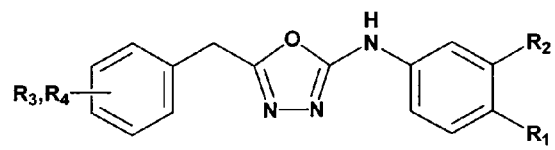

| Compd | R$_1$ | R$_2$ | R$_3$ | R$_4$ | EC$_{50}$[a] | CC$_{50}$[b] |
|---|---|---|---|---|---|---|
| 1 S10087 | CH$_3$ | H | 3-OCH$_3$ | 4-OCH$_3$ | NA | 61 |
| 11 JL0195 | Cl | H | 4-Cl | H | NA | >100 |
| 12 JL0196 | Cl | H | 3-Cl | H | >10 | 32 |
| 13 JL0197 | Cl | H | 3-CH$_3$ | 5-CH$_3$ | NA | >100 |
| 14 JL0198 | Cl | H | 2-Cl | 6-Cl | 0.82 | 20 |
| 15 JL0199 | Cl | H | H | H | NA | 31 |
| 16 JL0200 | H | H | H | H | NA | >100 |
| 17 JL0201 | Cl | CH$_3$ | 2-Cl | 6-Cl | 1.3 | >100 |
| 18 JL0202 | 2-Cl,4-Cl | OCH$_3$ | 2-Cl | 6-Cl | NA | 9 |
| 19 JL0203 | Cl | Cl | 2-Cl | 6-Cl | 0.31 | >100 |
| 20 JL0204 | Cl | CF$_3$ | 2-Cl | 6-Cl | NA | 9 |
| d4T | | | | | 1.6 | >100 |
| Nevirapine | | | | | 0.11 | >10 |

[a] For 50% protection in MT-2 cells; antiviral curves used triplicate samples at each concentration. NA for EC$_{50}$ > CC$_{50}$. [b] For 50% inhibition of MT-2 cell growth; toxicity curves also used triplicate samples.

FIGURE 8
Table 6 Oxadiazoles: Anti-HIV-1 Activity (EC$_{50}$) and Cytotoxicity (CC$_{50}$) in µM
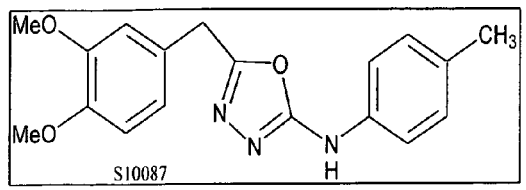 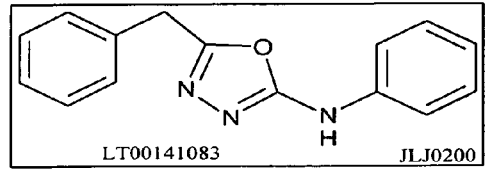
|  | EC$_{50}$ | CC$_{50}$ |
|---|---|---|
| S10087 | NA | 61 |
| LT00141083 JLJ0200 | NA | >100 |
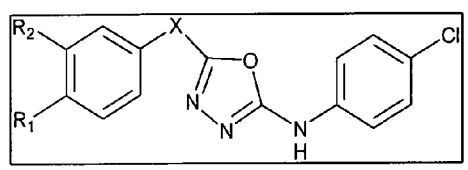 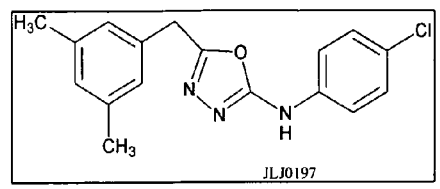
| Compound | X | R1 | R2 | EC50 | CC50 |
|---|---|---|---|---|---|
| JLJ0194 | NH | Cl | H | NA | 12 |
| JLJ0195 | CH2 | Cl | H | NA | >100 |
| JLJ0196 | CH2 | H | Cl | >10 | 32 |
| JLJ0199 | CH2 | H | H | NA | 31 |
| JLJ0197 | CH2 | 5-CH3 | CH3 | | |
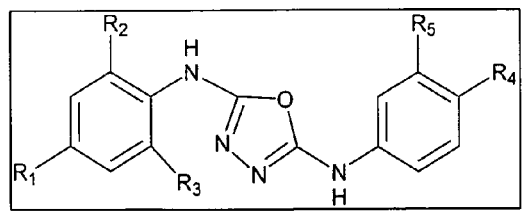 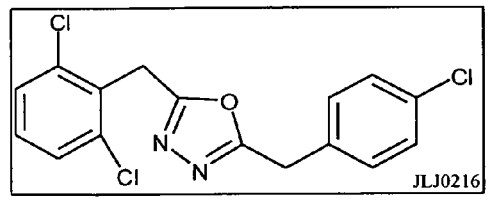
| Compound | R1 | R2 | R3 | R4 | R5 | EC50 | CC50 |
|---|---|---|---|---|---|---|---|
| JLJ0194 | Cl | H | H | Cl | H | NA | 12 |
| JLJ0209 | H | Cl | Cl | Cl | H | >100 | >100 |
| JLJ0210 | H | Cl | Cl | Cl | Cl | 22.00 | 62.00 |
| JLJ0211 | H | Cl | Cl | CN | H | 9.80 | >100 |
| JLJ0212 | CN | CH3 | CH3 | Cl | H | 34.00 | 100.00 |
| JLJ0216 | see Right Figure, above | | | | | 18.00 | 43.00 |

Table 7 Further Oxadiazoles: Anti-HIV-1 Activity ($EC_{50}$) and Cytotoxicity ($CC_{50}$) μM

| Compound | R1 | R2 | R3 | X | R4 | EC50 | CC50 |
|---|---|---|---|---|---|---|---|
| JLJ0209 | Cl | Cl | Cl | N | H | >100 | >100 |
| JLJ0211 | Cl | Cl | CN | N | H | 9.80 | >100 |
| JLJ0229 | Cl | Cl | CN | N | CH3 | 0.27 | 30.00 |
| Retest |  |  |  |  |  | 0.27 | >100 |
| JLJ0230 | Cl | Cl | CN | CH | CH3 | 1.20 | 18.00 |
| Retest |  |  |  |  |  | 1.20 | 54.00 |
| JLJ0231 | F | F | CN | CH | CH3 | 0.2 | 5.20 |
| Retest |  |  |  |  |  | 0.13 | 8.50 |
| JLJ0198 | Cl | Cl | Cl | CH | H | 0.82 | 20.00 |
| JLJ0213 | Cl | Cl | CN | CH | H | 0.13 | 40.00 |
| JLJ0232 | F | F | CN | CH | H | 0.36 | 20.00 |
| Retest |  |  |  |  |  | 0.23 | 90.00 |

FIGURE 10

Table 8 Further Oxadiazoles: Anti-HIV-1 Activity (EC$_{50}$) and Cytotoxicity (CC$_{50}$) µM

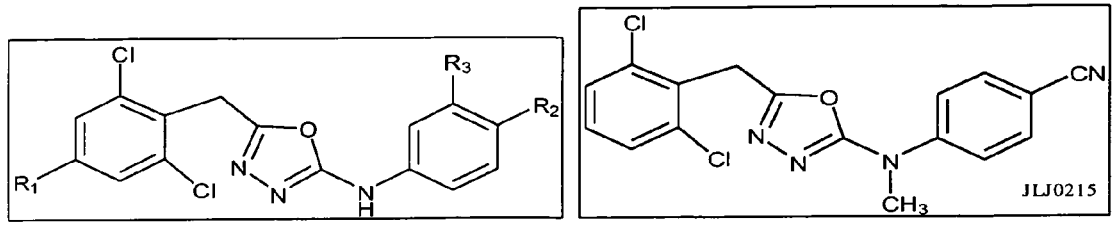

| Compound | R1 | R2 | R3 | EC50 | CC50 |
|---|---|---|---|---|---|
| JLJ0225 | H | H | 2-Cl | NA | >100 |
| JLJ0226 | H | H | Cl | 4.3 | 71 |
| JLJ0198 | H | Cl | H | 0.88 | 18 |
|  |  |  |  | 0.82 | 20 |
| JLJ0205 | H | Cl | 2-Cl | 2.4 | 45 |
| JLJ0203 | H | Cl | Cl | 0.31 | >100 |
| JLJ0214 | H | H | CN | 4.2 | 46 |
| JLJ0213 | H | CN | H | 0.25 | 42 |
|  | H | CN | H | 0.13 | 40 |
| JLJ0269 | H | CH3 | H | 3.8 | 99 |
| JLJ0201 | H | Cl | CH3 | 1.7 | >100 |
|  |  |  |  | 1.3 | >100 |
| JLJ0264 | H | CH2OH | H | 13 | 62 |
| JLJ0227 | H | CH2OCH3 | H | 4.3 | 100 |
| JLJ0228 | H | CH2OCH3 | Cl | 1.3 | 33 |
| JLJ0202 | H | Cl | "OCH3, 2-Cl" | NA | 9.4 |
| JLJ0204 | H | Cl | CF3 | NA | >100 |
| JLJ0215 | H | CN | see Figure | NA | 67 |
| JLJ0236 | H | CH2OCH2Ph | H | NA | 84 |
| Retest |  |  |  | NA | 81 |
| JLJ0237 | H | CH2OCH2-2-Fur | H | 3.1 | 9 |
| Retest |  |  |  | 2.8 | 12 |
| JLJ0263 | H | CH2OCH2-3-Fur | H | NA or 1? | 21 |
| JLJ0268 | H | CH2OCH2-3-Thienyl | H | NA | >100 |
| JLJ0267 | H | CH2OCH2-2-Pyrid | H | 5 | >100 |
| JLJ0261 | H | CH2OCH2-3-Pyrid | H | 4.6 | 81 |
| JLJ0262 | H | CH2OCH2-4-Pyrid | H | 2.3 | 6 |
| Retest |  |  |  | 1.6 | 81 |
| JLJ0243 |  | pyridinyl | see Figure 8B | NA | 100 |
| JLJ0250 |  | pyridine N-oxide | see Figure 8B | NA | >100 |

FIGURE 11
Compounds of Table 8 Figure 10
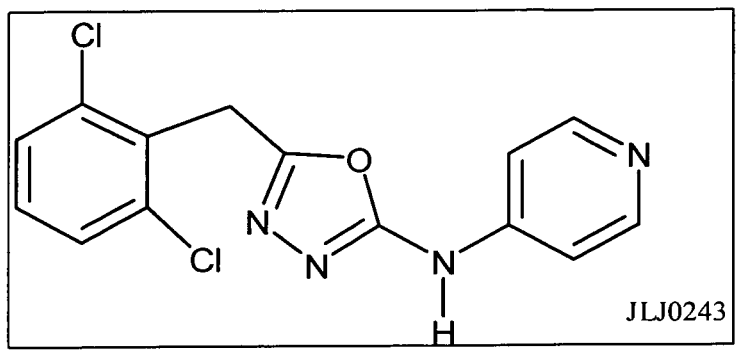
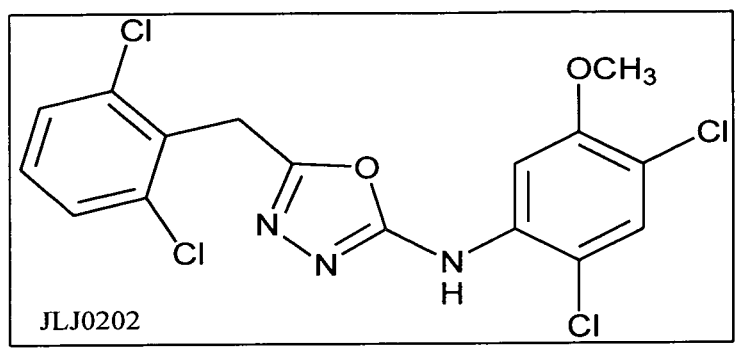
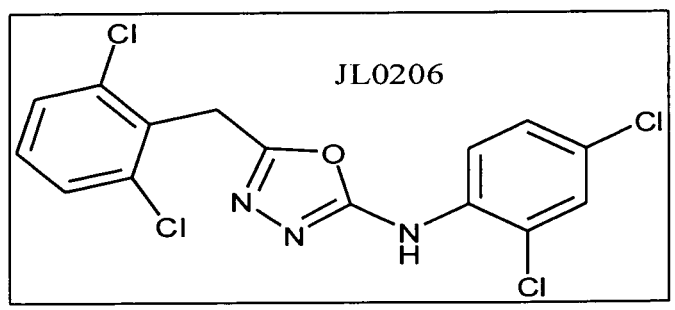
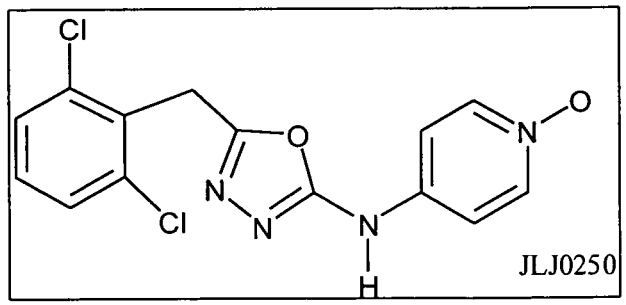

Table 9 Thiadiazoles/ Thiazoles Anti-HIV-1 Activity (EC$_{50}$) and Cytotoxicity (CC$_{50}$) µM

| Compound | R1 | R2 | R3 | "X, Y" | EC50 | CC50 |
|---|---|---|---|---|---|---|
| JLJ0198 | H | Cl | H | "N,O" | 0.82 | 20 |
| JLJ0213 | H | CN | H | "N,O" | 0.13 | 40 |
| JLJ0223 | H | H | "3,5-diCl" | "N, S" | NA | 64 |
| JLJ0224 | H | Cl | H | "N,S" | NA | >100 |
| JLJ0244 | H | Cl | Cl | "CH,S" | 1.4 | 9.8 |
| JLJ0233 | H | Cl | H | "CH,S" | 2.1 | 27 |
| Retest | | | | | 4.1 | 30 |
| JLJ0241 | H | H | "2,6-diCl" | "CH,S" | NA | 63.0 |
| JLJ0242 | H | CN | H | "CH,S" | 0.43 | >100 |

FIGURE 13
Table 10 Oxazoles Anti-HIV-1 Activity (EC$_{50}$) and Cytotoxicity (CC$_{50}$) µM
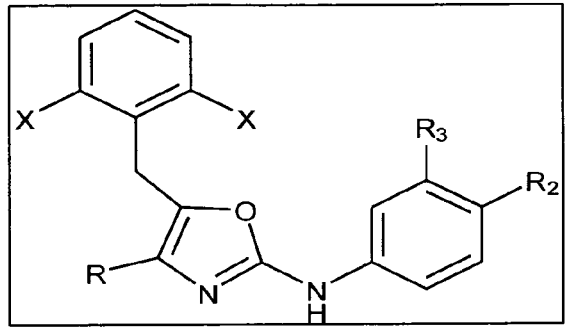
| Compound | X | R2 | R3 | R | EC50 | CC50 |
|---|---|---|---|---|---|---|
| JLJ0234 | Cl | Cl | H | | <0.2 | |
| Retest | | | | | 0.11 | 2.8 |
| JLJ0235 | Cl | CN | H | | <0.2 | |
| Retest | | | | | 0.022 | 2.1 |
| JLJ0238 | Cl | Et | H | | 2.8 | unc |
| JLJ0239 | Cl | F | H | | 0.43 | 12.0 |
| JLJ0240 | F | CN | H | | <0.2 | 16.0 |
| Retest | | | | | 0.013 | 7.4 |
| JLJ0245 | Cl | Me | H | | 1 | 47.0 |
| JLJ0246 | F | Me | H | | 0.9 | >100 |
| JLJ0247 | F | Et | H | | 1.4 | >100 |
| JLJ0248 | Cl | 3-Cl | 5-Cl | | NA | 19.0 |
| JLJ0249 | F | F | H | | 0.47 | 38.0 |
| JLJ0251 | Cl | COOMe | H | H | NA | >100 |
| JLJ0252 | F | COOMe | H | H | NA | 15.0 |
| JLJ0253 | Cl | CN | H | Me | <0.2 | 82.0 |
| Retest | | | | | 0.14 | >1 |
| Retest | | | | | 0.16 | >1 |
| JLJ0270 | F | CH2OCH3 | H | | | |
| JLJ0271 | Cl | CH2OCH3 | H | | | |
| CID7575754 | | See Figure Below | | | 6.2 | 37 |
CID7575754
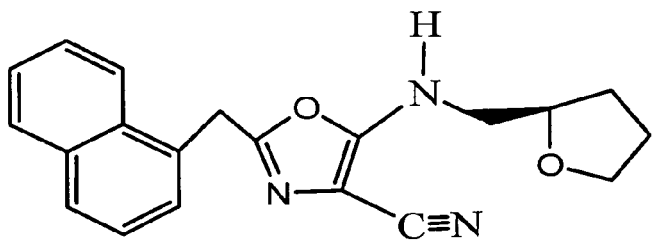

FIGURE 14
Additional Oxadiazole Compounds According to the Present Invention
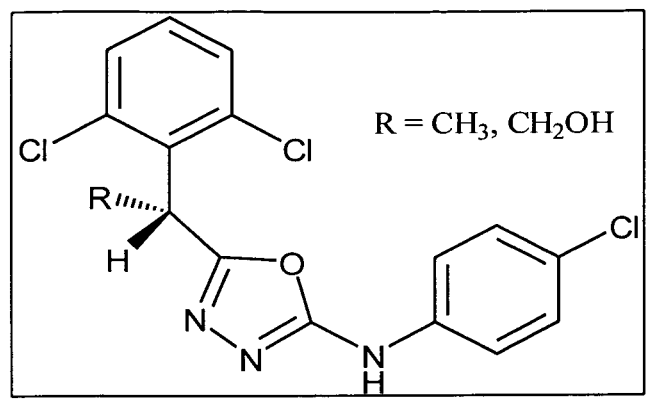
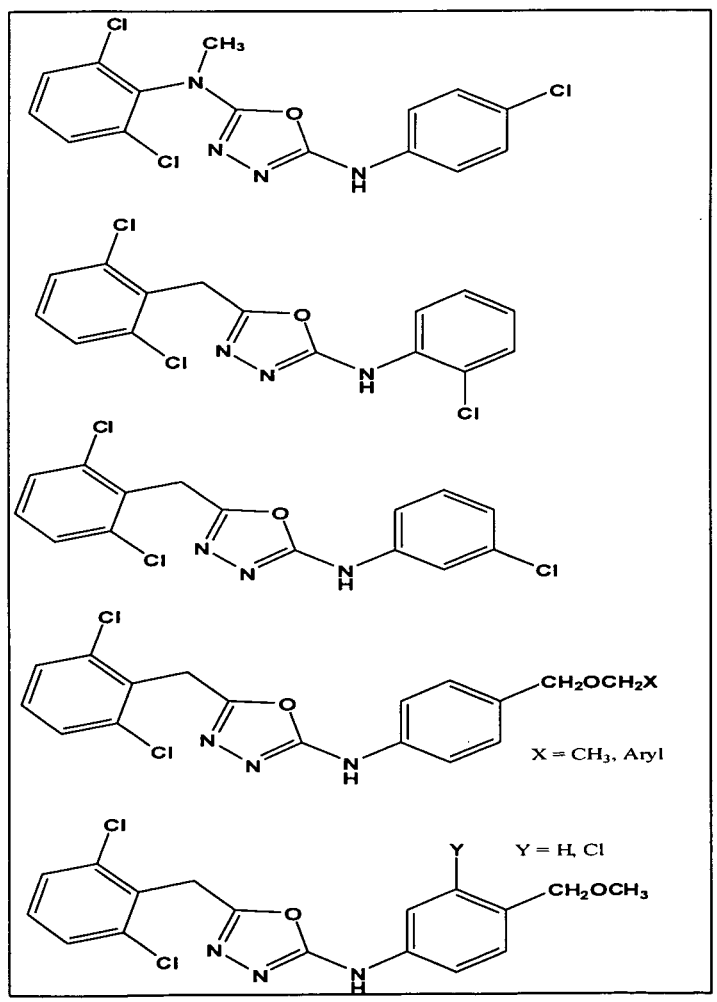

FIGURE 15
Additional Oxadiazole According to the Present Invention
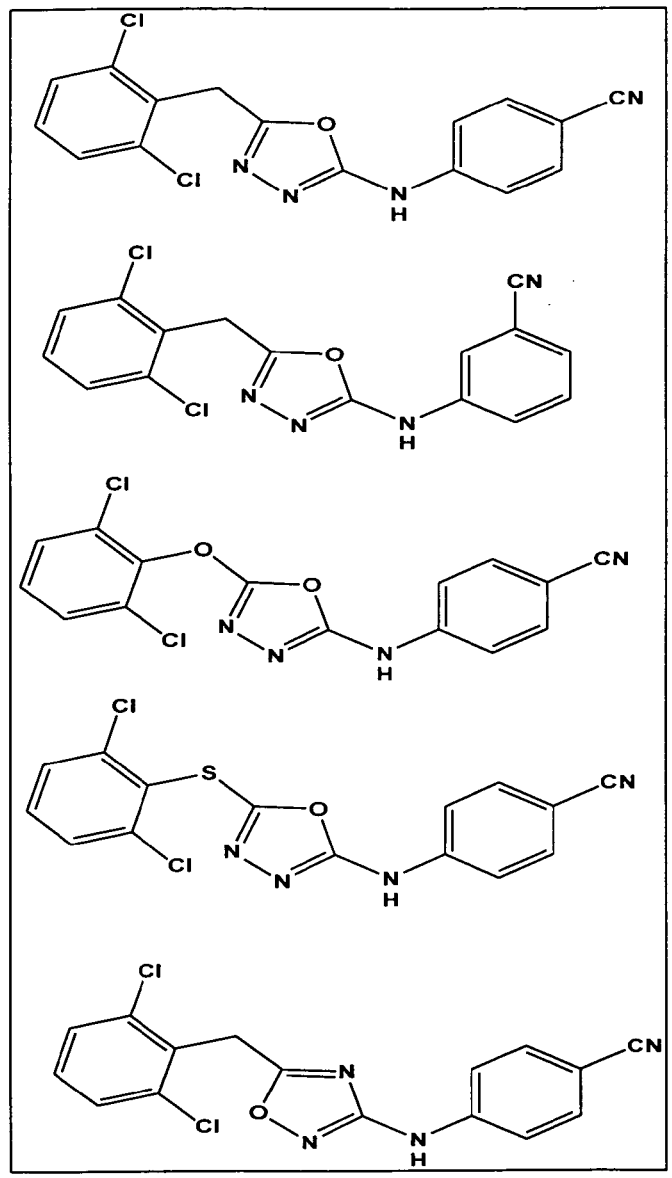
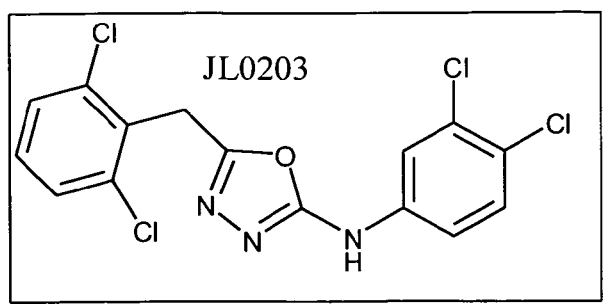

FIGURE 16
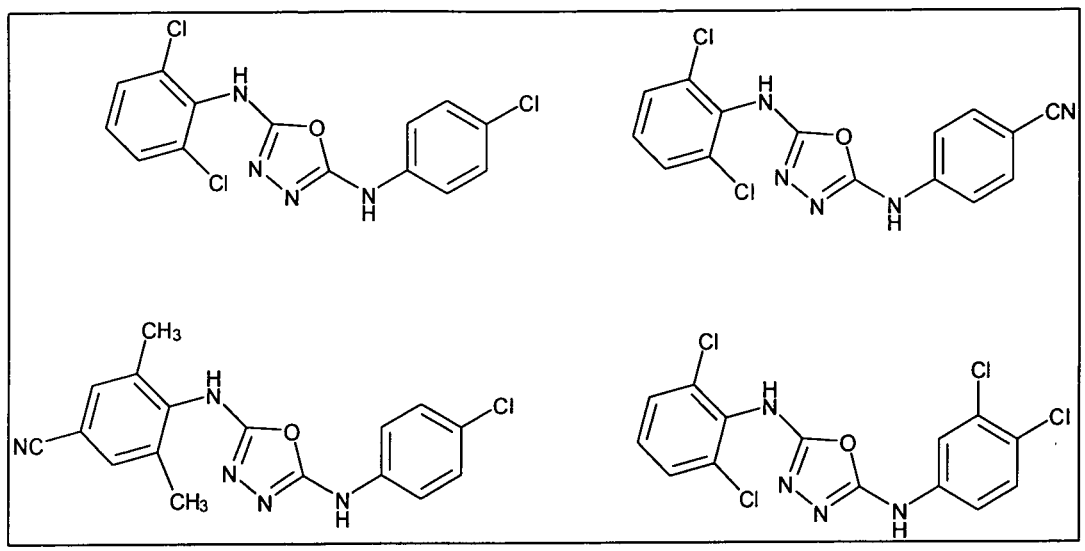
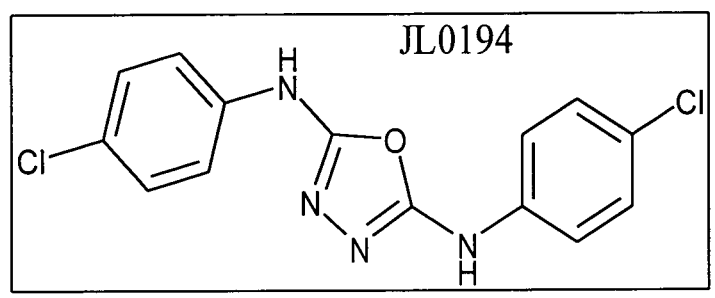
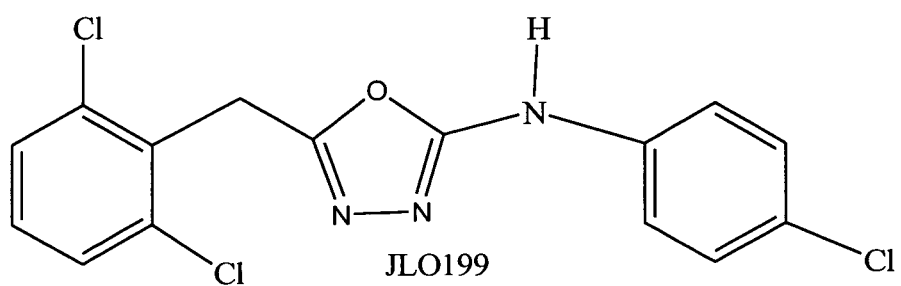

AZOLES AND RELATED DERIVATIVES AS NON-NUCLEOSIDE REVERSE TRANSCRIPTASE INHIBITORS (NNRTIS) IN ANTIVIRAL THERAPY (HIV)

RELATED APPLICATIONS

This application claims the benefit of priority of U.S. provisional application No. 60/958,392, filed Jul. 3, 2007, entitled "Novel Oxadiazole Derivatives as NNRTIs for Antiviral Therapy (HIV)" the entire contents of which is incorporated by reference herein.

This invention was made with government support under GM032136, AI044616, and GM049551 awarded by National Institute of Health. The government has certain rights in the invention.

FIELD OF THE INVENTION

The present invention relates to novel heterocyclic compounds, including oxadiazole and oxazole compounds, pharmaceutical compositions and their use in the inhibition of reverse transcriptase and the treatment of HIV (1 and 2) infections and other viral infections.

BACKGROUND OF THE INVENTION

The AIDS crisis continues with ca. 40 million people infected by HIV and 2.9 million HIV-related deaths in 2006.[1] The virally encoded proteins of HIV provide chemotherapeutic targets for the treatment of infection by the virus. A principal point of attack has been HIV reverse transcriptase (RT), which is required for the conversion of the viral genomic RNA to DNA and for successful infection of host cells. This has led to the development and FDA approval of two important classes of anti-HIV drugs: (i) nucleoside and nucleotide RT inhibitors (NRTIs and NtRTIs), e.g., AZT, ddI, ddC, d4T, FTC, TDF, and 3TC, and (ii) non-nucleoside RT inhibitors (NNRTIs), specifically, nevirapine, delavirdine, efavirenz (Sustiva) and atravirine (TMC125). The NRTIs and NtRTIs are actually faulty substrates that cause premature termination of the growing DNA transcript, while NNRTIs are true inhibitors which bind to an allosteric pocket in the vicinity of the polymerase active site. The therapeutic situation is challenged by rapid mutation of the virus to yield resistant strains. This leads to need for new drugs with activity against at least parts of the spectrum of variants, which are now clinically observed.

The present efforts have been directed at the development of NNRTIs with enhanced therapeutic spectra and auspicious pharmacological properties. The approach to-date has featured focused synthetic organic chemistry and anti-HIV assaying driven by automated procedures for creation and evaluation of virtual libraries, estimation of pharmacological properties, and lead optimization featuring free-energy perturbation calculations to assess relative protein-ligand binding affinities.[3] Highly potent and structurally diverse anti-HIV agents have been discovered, however, we continue to seek activity against an ever-wider range of viral mutants and exploration of alternative structural classes for NNRTIs.

To this end, reported successes for lead generation by molecular docking have been intriguing,[4] and it was decided to try this approach to seek novel NNRTIs. The following report provides a case study on a common dilemma in a virtual or high-throughput screening exercise. It is demonstrated that with confidence in computed structures and estimated activities, it is possible to convert a false positive into an active agent.

BRIEF DESCRIPTION OF THE FIGURES

FIG. 1 shows two generic chemical synthetic schemes for oxadiazole compounds according to the present invention.

FIG. 2 shows two generic chemical synthetic schemes for diamine oxadiazole compounds and oxazole compounds according to the present invention.

FIG. 3 shows the anti-HIV-1 activity ($EC_{50}$) and Cytotoxicity ($CC_{50}$) in µM, for a number of oxadiazole compounds which were synthesized and tested. In FIG. 3, table 1, the following legend applies:[a] For 50% protection in MT-2 cells; antiviral curves used triplicate samples at each concentration. NA for $EC_{50} > CC_{50}$.[b] For 50% inhibition of MT-2 cell growth; toxicity curves also used triplicate samples.

FIG. 4 shows the anti-HIV-1 activity ($EC_{50}$) and Cytotoxicity ($CC_{50}$) in µM, for a number of oxadiazole compounds which were synthesized and tested. In FIG. 4, table 2 the following legend applies:[a] For 50% protection in MT-2 cells; antiviral curves used triplicate samples at each concentration. NA for $EC_{50} > CC_{50}$. For 50% inhibition of MT-2 cell growth; toxicity curves also used triplicate samples.[b] Racemate.

FIG. 5, Table 3 shows the anti-HIV-1 activity ($EC_{50}$) and Cytotoxicity ($CC_{50}$) in µM, for a number of oxadiazole compounds which were synthesized and tested. In FIG. 5, table 3, the following legend applies:

[a]For 50% protection in MT-2 cells; antiviral curves used triplicate samples at each concentration. NA for $EC_{50} > CC_{50}$. For 50% inhibition of MT-2 cell growth; toxicity curves also used triplicate samples.

FIG. 6, Table 4 shows the anti-HIV-1 activity ($EC_{50}$) and Cytotoxicity ($CC_{50}$) in µM, for a number of azole compounds which were synthesized and tested against Wild-type and mutant strains of HIV (Y181C and K103N/Y181C. In FIG. 6, table 4, the following legend applies:[a] For 50% protection in MT-2 cells; antiviral curves used triplicate samples at each concentration. NA for $EC_{50} > CC_{50}$. For 50% inhibition of MT-2 cell growth; toxicity curves also used triplicate samples.

FIG. 7, Table 5 shows the anti-HIV-1 activity ($EC_{50}$) and Cytotoxicity ($CC_{50}$) in µM, for a number of oxadiazole compounds which were synthesized and tested. In FIG. 7, table 5, the following legend applies:

[a]For 50% protection in MT-2 cells; antiviral curves used triplicate samples at each concentration. NA for $EC_{50} > CC_{50}$. For 50% inhibition of MT-2 cell growth; toxicity curves also used triplicate samples.

Figure 9:
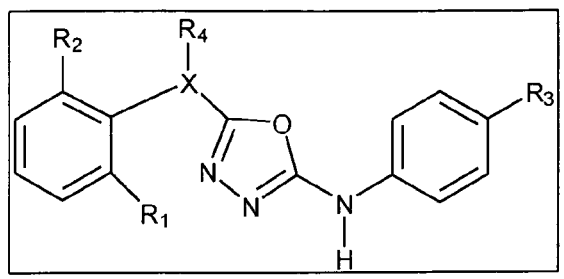

FIGS. 8-10 show the anti-HIV-1 activity ($EC_H$) and Cytotoxicity ($CC_{50}$) in µM, for a number of oxadiazole compounds which were synthesized and tested in Tables 6, 7 and 8. In FIGS. 8-10, the following legend applies:[a] For 50% protection in MT-2 cells; antiviral curves used triplicate samples at each concentration. NA for $EC_{50} > CC_{50}$. For 50% inhibition of MT-2 cell growth; toxicity curves also used triplicate samples.

FIG. 11 shows several compounds which were presented in Table 8, FIG. 10.

Figure 12:
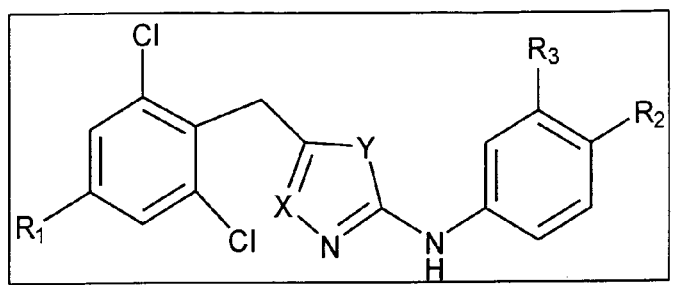
Figure 17:
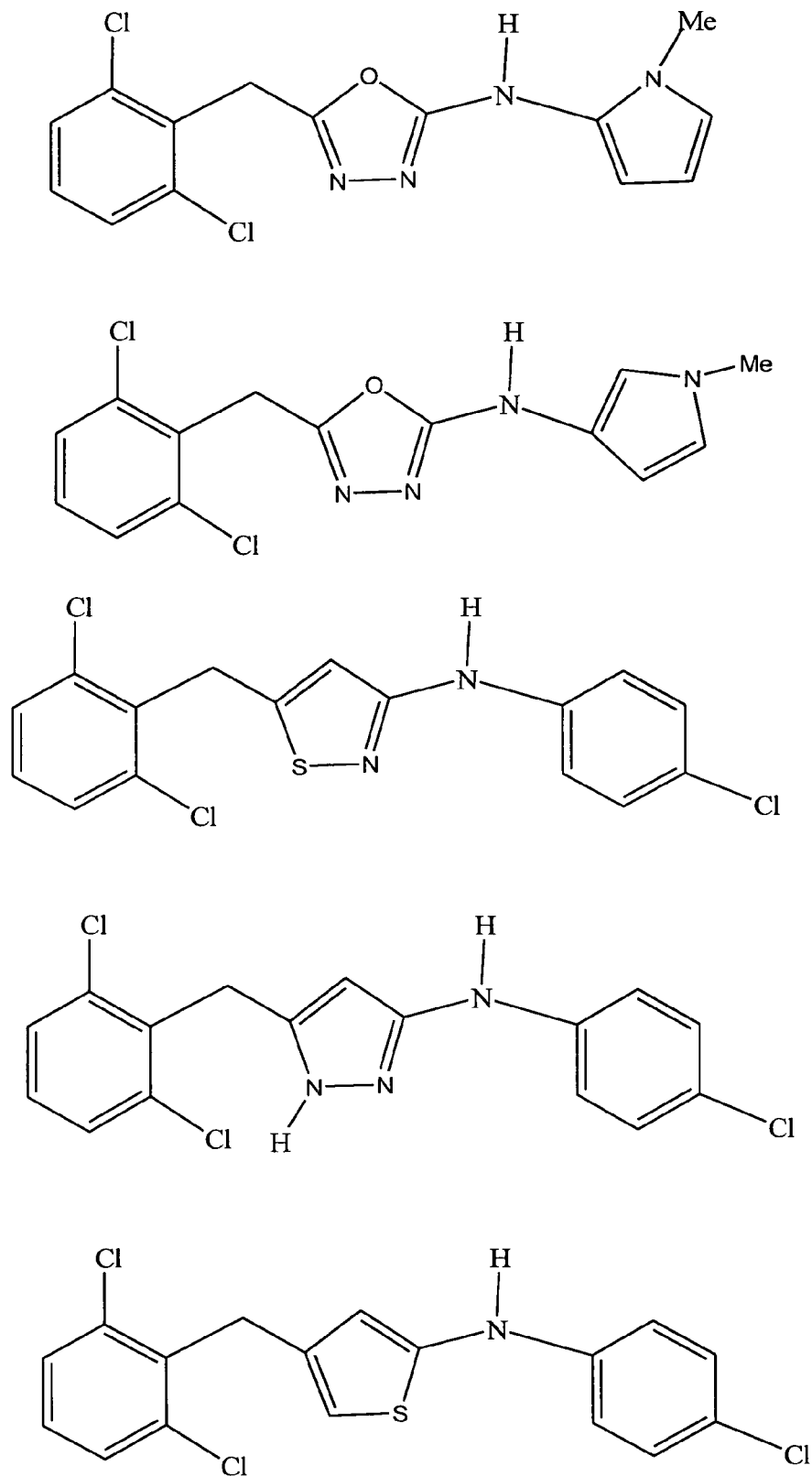

FIG. 12 shows the anti-HIV-1 activity ($EC_{50}$) and Cytotoxicity ($CC_{50}$) in µM, for a number of thiadiazole/thiazole compounds which were synthesized and tested. In FIG. 12, table 9, the following legend applies:

*For 50% protection in MT-2 cells; antiviral curves used triplicate samples at each concentration. NA for $EC_{50} > CC_{50}$. For 50% inhibition of MT-2 cell growth; toxicity curves also used triplicate samples.

FIG. 13 shows the anti-HIV-1 activity ($EC_{50}$) and Cytotoxicity ($CC_{50}$) in μM, for a number of oxazole compounds which were synthesized and tested. In FIG. 13, table 10, the following legend applies:

*For 50% protection in MT-2 cells; antiviral curves used triplicate samples at each concentration. NA for $EC_{50} > CC_{50}$. For 50% inhibition of MT-2 cell growth; toxicity curves also used triplicate samples.

FIGS. 14-17 show additional compounds which were synthesized and represent preferred embodiments according to the present invention.

SUMMARY OF THE INVENTION

The present invention is directed to compounds according to the chemical structure:

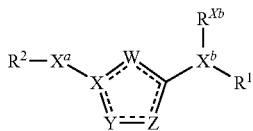

Where W is $N-N^{WNa}$, O, S, or $CR^aR^b$;
X is N or C;
Y is $N-R^{YNa}$, O, S or $CR^aR^b$;
Z is $N-R^{ZNa}$, O, S or $CR^aR^b$; with the proviso that W, Y and Z are not simultaneously $CR^aR^b$;
$R^{WNa}$ is absent (N is $-N=$, thus forming a double bond with an adjacent atom); H or an optionally substituted $C_1$-$C_3$ alkyl;
$R^{YNa}$ is absent (N is $-N=$, thus forming a double bond with an adjacent atom), H or an optionally substituted $C_1$-$C_3$ alkyl;
$R^{ZNa}$ is absent (N is $-N=$, thus forming a double bond with an adjacent atom), H or an optionally substituted $C_1$-$C_3$ alkyl;
$R^a$ is absent (C is $-C=$, thus forming a double bond with an adjacent atom), H, or an optionally substituted $C_1$-$C_3$ alkyl (preferred substituents are methyl and cyano);
$R^b$ is H, CN, or an optionally substituted $C_1$-$C_3$ alkyl, preferably not more than one $R^b$ is CN (preferred substituents being methyl and cyano);
$X^a$ is $N-R^{NXa}$, $CR^{ba}R^{ba}$, O or S, preferably $X^a$ is $CR^{ba}R^{ba}$;
$R^{NXa}$ is H or an optionally substituted $C_1$-$C_3$ alkyl group;
$R^{ba}$ is H or an optionally substituted $C_1$-$C_3$ alkyl, preferably $R^{ba}$ is H
$X^b$ is N, $C-R^{Xba}$; O or S;
$R^{Xb}$ is absent (when $X^b$ is O or S), H, or an optionally substituted $C_1$-$C_3$ alkyl (preferably H);
$R^{Xba}$ is H, or an optionally substituted $C_1$-$C_3$ alkyl (preferably H);
$R^1$ is an optionally substituted carbocyclic or heterocyclic group, preferably an aromatic group, preferably $R^1$ is a phenyl group which is optionally substituted with up to four substituents which are preferably selected from the group consisting of hydroxyl (OH), halogen (preferably F or Cl), CN, $NO_2$, a $C_1$-$C_6$ optionally substituted alkyl group (preferably $CH_3$, $CH_2CH_3$ or $CF_3$), a $C_1$-$C_6$ alkoxy group (which group may contain an unsaturated hydrocarbon), a $C_2$-$C_6$ ether, group (which group may contain an unsaturated hydrocarbon); and
$R^2$ is an optionally substituted carbocyclic or heterocyclic group, preferably an aromatic group, preferably $R^1$ is a phenyl group which is optionally substituted with up to four substituents which are preferably selected from the group consisting of hydroxyl, halogen (preferably F or Cl), CN, $NO_2$, a $C_1$-$C_6$ optionally substituted alkyl group (preferably $CH_3$, $CH_2CH_3$ or $CF_3$), a $C_1$-$C_6$ alkoxy group (which group may contain an unsaturated hydrocarbon), a $C_2$-$C_6$ ether group (which group may contain an unsaturated hydrocarbon);

or a pharmaceutically acceptable salt, enantiomer, stereoisomer, solvate or polymorph, thereof.

Preferably, in the above generic formula, Z is $N-R^{ZNa}$ and $R^{ZNa}$ is absent (N forms a double bond with an adjacent atom) or Z is $CR^aR^b$; where $R^a$ is absent and $R^b$ is CN. In other preferred aspects of the invention, X is $-C=$ and $X^a$ is preferably $CH_2$. In other preferred aspects of the invention, Y is $N-R^{YNa}$ or $CR^aR^b$ wherein $R^{YNa}$ and $R^a$ are absent. $R^{ba}$ is preferably H. $X^a$ is preferably $CR^{ba}R^{ba}$ such that $X^a$ is $CH_2$ and $X^b$ is preferably N. $R^{Xb}$ is preferably H. W is preferably O or S, more preferably O. Preferably, $R^1$ is a phenyl group or 3-6-membered carbocyclic or heterocyclic group (which can be saturated or unsaturated) which is optionally substituted with up to four substituents, preferably no more than three substituents which are selected from F, Cl, Br, CN, $NO_2$, an optionally substituted alkyl group ($CH_3$, $CH_2CH_3$, $CH_2OH$, $CH_2CH_2OH$ or $CF_3$), a $C_1$-$C_6$ alkoxy group (which group may contain an unsaturated hydrocarbon), a $C_2$-$C_6$ ether group (which group may contain an unsaturated hydrocarbon), a $C_2$-$C_6$ ester group, or an optionally substituted aryl (including heteroaryl) group (phenyl, thienyl, pyridyl, furanyl, among others); and $R^2$ is an optionally substituted phenyl group which is substituted with no more than three substituents which are selected from OH, F, Cl, CN, $NO_2$, an optionally substituted alkyl group ($CH_3$, $CH_2CH_3$, $CH_2OH$, $CH_2CH_2OH$ or $CF_3$), a $C_1$-$C_6$ alkoxy group (which group may contain an unsaturated hydrocarbon), a $C_2$-$C_6$ ether group (which group may contain an unsaturated hydrocarbon, especially an alkene), a $C_2$-$C_6$ ester group, or an optionally substituted aryl (including heteroaryl) group (phenyl, thienyl, pyridyl, furanyl, among others), especially $CH_2OCH_2$-furanyl, $CH_2OCH_2$-pyridyl, pyridine-N-oxide, pyrimidyl and optionally substituted phenyl, including benzyl $CH_2OCH_2$-phenyl.

In more particular aspects of the present invention, compounds according to the present invention have the following chemical structure:

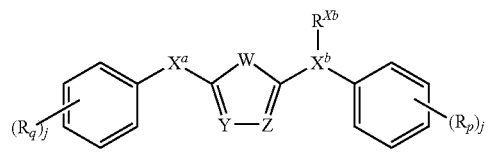

Where W is O or S;
Y is N or $C-R^b$, preferably Y is N or CH;
Z is N or $-C-R^b$, preferably Z is N or $-C-R^b$ is $C-CN$;
$R^b$ is H, CN or an optionally substituted $C_1$-$C_3$ alkyl;
$X^a$ is $N-R^{NXa}$, $CR^{ba}R^{ba}$, O or S, preferably $X^a$ is $CR^{ba}R^{ba}$ and $R^{ba}$ is H;
$R^{NXa}$ is H or an optionally substituted $C^1$-$C^3$ alkyl group;
$X^b$ is N or $C-R^{Xba}$, preferably N;
$R^{Xb}$ is H, or an optionally substituted $C_1$-$C_3$ alkyl, preferably H;
$R^{Xba}$ is H, or an optionally substituted $C_1$-$C_3$ alkyl, preferably H;

Each $R_p$ and $R_q$ is independently selected from the group consisting of hydroxyl, carboxyl, cyano (C≡N), nitro ($NO_2$), halogen (preferably, 1, 2 or 3 halogens, especially on an alkyl, especially a methyl group such as a trifluoromethyl), thiol, an optionally substituted alkyl, alkene or alkyne group (preferably, $C_1$-$C_6$, $C_2$-$C_6$, more preferably $C_1$-$C_3$, $C_2$-$C_3$), optionally substituted aryl (especially optionally substituted phenyl or benzyl), optionally substituted heterocyclic (especially optionally substituted heteroaryl for example, pyridyl (2-, 3-, 4-), pyrimidinyl, thienyl (2- or 3-) or furanyl (2- or 3-), alkoxy (preferably, $C_1$-$C_6$ alkyl or aryl), optionally substituted ether (preferably, $C_1$-$C_{10}$ alkyl ether, alkenylether, alkynyl ether or aryl ether, including phenyl or benzyl ether), optionally substituted acyl (preferably $C_2$-$C_8$ acyl which may include an aryl substituted acyl or a trifluoroacetyl), optionally substituted ester (preferably, $C_1$-$C_6$ alkyl or aryl) including alkylene, alkenyl or alkynyl ester (alkylene attachment to compound), ketoester (carbonyl attachment to compound) or hydroxyester (oxygen attachment to compound), thioether (preferably, $C_1$-$C_6$ alkyl or aryl), thioester (preferably, $C_1$-$C_6$ alkyl or aryl), amine (including a five- or six-membered cyclic alkylene amine, including an optionally substituted $C_1$-$C_6$ alkyl amine, e.g., monoalkanolamine) or an optionally substituted $C_1$-$C_6$ dialkyl amine (e.g. dialkanolamine), alkanol (preferably, $C_1$-$C_6$ alkyl or aryl), or alkanoic acid (preferably, $C_1$-$C_6$ alkyl or aryl), optionally substituted carboxyamide (carbonyl attached to the carbon atom with one or two substituents on the amine group—preferably H or an optionally substituted $C_1$-$C_6$ alkyl group), amido group (amine group with H or $C_1$-$C_3$ alkyl group attached to the carbon atom with a single group, preferably H or an optionally substituted $C_1$-$C_6$ alkyl group on the keto group) or an optionally substituted urethane group (with either the amine or the O-carboxy group attached to a carbon atom to which the urethane is a substituent—the amine group being substituted with one or two H or one or two $C_1$-$C_6$ alkyl groups);

j is 0, 1, 2, 3 or 4, preferably 1, 2 or 3;

or a pharmaceutically acceptable salt, enantiomer, stereoisomer, solvate or polymorph, thereof.

In further preferred aspects of the invention, $R_p$ and $R_q$ are independently selected form the group consisting of F, Cl, Br, CN, $NO_2$, an optionally substituted alkyl group ($CH_3$, $CH_2CH_3$, $CH_2OH$, $CH_2CH_2OH$ or $CF_3$), a $C_1$-$C_6$ alkoxy group (which group may contain an unsaturated hydrocarbon), a $C_2$-$C_6$ ether group (which group may contain an unsaturated hydrocarbon), a $C_2$-$C_6$ ester group, or an optionally substituted aryl (including heteroaryl) group (phenyl, especially benzyl, thienyl, pyridyl, furanyl, among others); and $R^2$ is an optionally substituted phenyl group which is substituted with no more than three substituents which are selected from F, Cl, CN, $NO_2$, an optionally substituted alkyl group ($CH_3$, $CH_2CH_3$, $CH_2OH$, $CH_2CH_2OH$ or $CF_3$), a $C_1$-$C_6$ alkoxy group (which group may contain an unsaturated hydrocarbon), a $C_2$-$C_6$ ether group (which group may contain an unsaturated hydrocarbon), a $C_2$-$C_6$ ester group, or an optionally substituted aryl (including heteroaryl) group (phenyl, especially benzyl, thienyl, pyridyl, furanyl, among others), especially $CH_2OCH_2$-furanyl, $CH_2OCH_2$-pyridyl, pyridine N-oxide, pyrimidyl and optionally substituted phenyl. Particularly preferred substituents include halogen (especially fluoro and chloro), $CH_3$, $CH_2CH_3$, $CF_3$, $CH_2OH$, $CH_2OCH_3$, $OCH_3$, CN, benzyl, thienyl, pyridyl, furanyl, among other heteroaryl groups), especially $CH_2OCH_2$-furanyl, $CH_2OCH_2$-pyridyl, $CH_2OCH_2$-thienyl, pyrimidyl and optionally substituted phenyl.

In another embodiment according to the present invention, pharmaceutical compositions comprise an effective amount of one or more compounds as described above, optionally in combination with a pharmaceutically acceptable carrier, excipient or additive. Pharmaceutical compositions may also include, in addition to the present compounds, at least one additional compound, including another anti-HIV agent which inhibits HIV by a mechanism other than through reverse transcriptase inhibition, although other reverse transcriptase inhibitors may be used, especially nucleoside reverse transcriptase inhibitors (NRTIs).

In yet another embodiment, the present application is directed to the treatment HIV infections, including the treatment of AIDS and ARC, said method comprising administering to a patient in need thereof an effective amount of a pharmaceutical composition comprising any one or more of the compounds previously described above, optionally in combination (coadministered) with another active agent, preferably another anti-HIV agent as otherwise disclosed herein.

DETAILED DESCRIPTION OF THE INVENTION

The following terms shall be used to describe the present invention. In cases where a term is not specifically defined herein, the term shall be given a common meaning used by those of ordinary skill in the art consistent with the use of that term within the context of describing the present invention.

As used herein and in the appended claims, the singular forms "a," "an," and "the" include plural reference unless the context clearly dictates otherwise. Thus, for example, a reference to "a compound" or other element of the present invention includes a plurality (for example, two or more elements) of such elements, and so forth. Under no circumstances is the patent to be interpreted to be limited to the specific examples or embodiments or methods specifically disclosed herein.

The term "compound", as used herein, unless otherwise indicated, refers to any specific chemical compound disclosed herein and includes tautomers, regioisomers, geometric isomers, and where applicable, optical isomers thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds.

The symbol ══ is used in chemical compounds according to the present invention to signify that a bond between atoms is a single bond or double bond according to the context of the bond's use in the compound, which depends on the atoms (and substituents) used in defining the present compounds. Thus, where a carbon (or other) atom is used and the context of the use of the atom calls for a double bond or single bond to link that atom with an adjacent atom in order to maintain the appropriate valence of the atoms used, then that bond is considered a double bond or a single bond.

The term "patient" or "subject" is used throughout the specification within context to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective" is used herein, unless otherwise indicated, to describe an amount of a compound or composition which, in context, is used to produce or effect an intended result, whether that result relates to the treatment of a viral, microbial or other disease state, disorder or condition associated with HIV, ARC or AIDS or alternatively, is used to produce another compound, agent or composition. This term subsumes all other effective amount or effective concentration terms which are otherwise described in the present application.

"Hydrocarbon" or "hydrocarbyl" refers to any monovalent (or divalent in the case of alkylene groups) radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups, including aromatic groups both substituted and unsubstituted, alkene groups (containing double bonds between two carbon atoms) and alkyne groups (containing triple bonds between two carbon atoms). In certain instances, the terms substituted alkyl and alkylene are sometimes synonymous.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups. "Alkylene" refers to a fully saturated hydrocarbon which is divalent (may be linear, branched or cyclic) and which is optionally substituted. Preferred alkylene groups are $C_1$-$C_6$ alkylene groups. Other terms used to indicate substituent groups in compounds according to the present invention are as conventionally used in the art.

"Aryl" or "aromatic", in context, refers to a substituted or unsubstituted monovalent aromatic radical having a single ring (e.g., benzene) or multiple condensed rings (e.g., naphthyl, anthracenyl, phenanthryl) and can be can be bound to the compound according to the present invention at any position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, pyridyl, furanyl, thiene, thiazole, pyridine, pyrimidine, pyrazine, triazole, oxazole, indole or fused ring systems (bicyclic, tricyclic), among others, which may be substituted or unsubstituted as otherwise described herein.

The term "cyclic" shall refer to an optionally substituted carbocyclic or heterocyclic group, preferably a 5- or 6-membered ring or fused rings (two or three rings) preferably containing from 8 to 14 atoms. A heterocyclic ring or group shall contain at least one monocyclic ring containing between 3 and 7 atoms of which up to four of those atoms are other than carbon and are selected from nitrogen, sulfur and oxygen. Carbocyclic and heterocyclic rings according to the present invention may be unsaturated or saturated. Preferred carbocyclic groups are unsaturated, and include phenyl groups, among other groups. Preferred heterocyclic groups are heteroaryl or heteroaromatic.

The term "heterocyclic group" as used throughout the present specification refers to an aromatic or non-aromatic cyclic group having 3 to 14 atoms, preferably 5 to 14 atoms forming the cyclic ring(s) and including at least one hetero atom such as nitrogen, sulfur or oxygen among the atoms forming the cyclic ring, which is an aromatic heterocyclic group (also, "heteroaryl" or "heteroaromatic") in the former case and a "non-aromatic heterocyclic group" in the latter case. Specific examples of the heterocyclic group therefore include specific examples of the aromatic heterocyclic group and specific examples of the non-aromatic heterocyclic group, both of which groups fall under the rubric "heterocyclic group" as otherwise described herein. Among the heterocyclic groups which may be mentioned for use in the present invention within context include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 14-membered heterocyclic groups and all subsets of heterocyclic groups (including non-heteroaromatic or heteroaromatic) subsumed under the definition of heterocyclic group.

Among the heterocyclic groups for use in the present invention may preferably include pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, pyridine-N-oxide, thiophene, benzothiophene, thiazole, benzothiazole, quinoline, quinazoline, cinnoline and carbostyryl, and even more preferably thiazole, quinoline, quinazoline, cinnoline and carbostyryl, among others.

Among the bicyclic or tricyclic heterocyclic groups which may be used in the present invention include indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "substituted" shall mean substituted at a carbon (or nitrogen) position within context, hydroxyl, carboxyl, cyano (C≡N), nitro (NO$_2$), halogen (preferably, 1, 2 or 3 halogens, especially on an alkyl, especially a methyl group such as a trifluoromethyl), thiol, an optionally substituted alkyl, alkene or alkyne group (preferably, $C_1$-$C_6$, $C_2$-$C_6$, more preferably $C_1$-$C_3$, $C_2$-$C_3$), optionally substituted aryl (especially optionally substituted phenyl or benzyl), optionally substituted heterocyclic (especially optionally substituted heteroaryl for example, pyridyl (2-, 3-, 4-), pyrimidinyl, thienyl (2- or 3-), furanyl (2- or 3-), alkoxy (preferably, $C_1$-$C_6$ alkyl or aryl), optionally substituted ether (preferably, $C_1$-$C_{10}$ alkyl ether, alkenylether, alkynyl ether or aryl ether, including phenyl or benzyl ether), acyl (preferably $C_2$-$C_8$ acyl which may include an aryl substituted acyl), optionally substituted ester (preferably, $C_1$-$C_6$ alkyl or aryl) including alkylene, alkenyl or alkynyl ester (alkylene attachment to compound), ketoester (carbonyl attachment to compound) or hydroxyester (oxygen attachment to compound), thioether (preferably, $C_1$-$C_6$ alkyl or aryl), thioester (preferably, $C_1$-$C_6$ alkyl or aryl), amine (including a five- or six-membered cyclic alkylene amine, including an optionally substituted $C_1$-$C_6$ alkyl amine (e.g., monoalkanolamine) or an optionally substituted $C_1$-$C_6$ dialkyl amine (e.g. dialkanolamine), alkanol (preferably, $C_1$-$C_6$ alkyl or aryl), or alkanoic acid (preferably, $C_1$-$C_6$ alkyl or aryl), optionally substituted carboxyamide (carbonyl attached to the carbon atom with one or two substituents on the amine group—preferably H or an optionally substituted $C_1$-$C_6$ alkyl group), amido group (amine group with H or $C_1$-$C_3$ alkyl group attached to the carbon atom with a single group, preferably H or an optionally substituted $C_1$-$C_6$ alkyl group on the keto group) or an optionally substituted urethane group (with either the amine or the O-carboxy group attached to a carbon atom to which the urethane is a substituent—the amine group being substituted with one or two H or one or two $C_1$-$C_6$ alkyl groups). Preferably, the term "substituted" shall mean within the context of its use alkyl, alkoxy, halogen, hydroxyl, carboxylic acid, cyano, ether, ester, acyl, nitro, amine (including mono- or di-alkyl substituted amines) and amide, as otherwise described above. Any substitutable position in a compound according to the present invention may be substituted in the present invention (including at linking groups, such as $X^a$ and $X^b$, among others). Preferably no more than 5, more preferably no more than 3 substituents are present on a single ring or ring system. Preferably, the term "unsubstituted" shall mean substituted with one or more H atoms. It is noted that in describing a substituent, all stable permutations of the substituent are intended.

Preferred substituents for use in the present invention include, for example, F, Cl, CN, NO$_2$, CH$_3$, CH$_2$OH, CH$_2$CH$_3$, CH$_2$OCH$_3$, CF$_3$, CO$_2$CH$_3$, optionally substituted thienyl, optionally substituted furanyl (especially CH$_2$OCH$_2$-furanyl), optionally substituted pyridyl (especially CH$_2$OCH$_2$-pyridyl), optionally substituted pyrimidyl and optionally substituted phenyl, including benzyl (CH$_2$OCH$_2$-phenyl).

The term "human immunodeficiency virus" shall be used to describe human immunodeficiency virus I (HIV 1 and 2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents, including, in particular, HIV strains which are resistant to one or more NRTI compounds and/or NNRTI compounds. Exemplary HIV drug resistant strains which may be effectively treated using compounds according to the present invention include the following, among others: (defined by RT mutation)-XXBRU, K65R, Y115F, F116Y, Q151M, M184V, L74V, V75T, 4XZT, T215Y, K103N, T215Y/M184V, 5705-72, 488-101, C910-6, LA1M184V, G910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H among others.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A category 2 (ARC) infection is characterized by the following criteria: The patient's T-cells have dropped below 500 but never below 200, and that patient has never had any Category 3 diseases (as set forth below) but have had at least one of the following defining illnesses—

Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ
Constitutional symptoms, such as fever (38.5 C) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess
Peripheral neuropathy According to the U.S. government, in Category 2 ARC, the immune system shows some signs of damage but it isn't life-threatening.

A Category 3 (AIDS) infection is characterized by the following criteria:

Your T-cells have dropped below 200 or
You have had at least one of the following defining illnesses—
Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)
Cytomegalovirus retinitis (with loss of vision)
Encephalopathy, HIV-related Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
*Pneumocystis carinii* pneumonia
Pneumonia, recurrent**
Progressive multifocal leukoencephalopathy
*Salmonella* septicemia, recurrent
Toxoplasmosis of brain
Wasting syndrome due to HIV The term "pharmaceutically acceptable" refers to a carrier, additive or excipient which is not unacceptably toxic to the subject to which it is administered. Pharmaceutically acceptable excipients are described at length by E.W. Martin, in "Remington's Pharmaceutical Sciences", among others well-known in the art.

A "pharmaceutically acceptable salt" of the present compound generally refers to pharmaceutically acceptable salts form of a compound which can form a salt, because of the existence of for example, amine groups, carboxylic acid groups or other groups which can be ionized in a sample acid-base reaction. A pharmaceutically acceptable salt of an amine compound, such as those contemplated in the current invention, include, for example, ammonium salts having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups or other acidic groups which may form pharmaceutically acceptable salts, for example, as carboxylate salts, are also contemplated by the present invention.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "inhibitory effective concentration" or "inhibitory effective amount" is used throughout the specification to describe concentrations or amounts of compounds according to the present invention which substantially or significantly inhibit the growth or replication of susceptible viruses, especially including human immunodeficiency viruses 1 and 2 (HIV-1 and HIV-2).

The term "preventing effective amount" is used throughout the specification to describe concentrations or amounts of compounds according to the present invention which are prophylactically effective in preventing, reducing the likelihood of infection or delaying the onset of infections in patients caused by human immunodeficiency viruses 1 and 2 (HIV-1 and HIV-2) and other viruses. The terms inhibitory effective amount or preventive effective amount also generally fall under the rubric "effective amount".

The term "coadministration" is used to describe the administration of two active compounds, in this case a compound according to the present invention, in combination with an additional anti-HIV agent or other biologically active agent, in effective amounts. Although the term coadministration preferably includes the administration of two active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

Compounds according to the present invention may be administered with one or more anti-viral agent, including other anti-HIV agents including nucleoside reverse transcriptase inhibitors (NRTI), other non-nucloeoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other agents which may be used in coadministration with compounds according to the present invention include, for example, other NNRTI's (i.e., other than the NNRTI's according to the present invention) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2-methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), 5C13PhS-2IndolCONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyly)carbonyl]-4-[3-(isopropylamino)-2-pyridinyl]piperazine (piperazine1 pyridine 4 indolyl derivative), 1-[5-[[N-(methyl)methylsulfonylamino]-2-indolylcarbonyl-4-[3-(isopropylamino)-2-pyridinyl] piperazine (piperazine 1pyridine 5 indolyl derivative), 1-[3-(Ethylamino)-2-[pyridinyl]-4-[(5-hydroxy-2-indolyl) carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]hiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4, 7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

Coadministration also includes the administration of other non anti-viral agents which may be beneficial for patients with HIV, AIDS or ARC.

Compounds according to the present invention may be used in pharmaceutical compositions having biological/pharmacological activity for the treatment of, for example, viral infections, as well as a number of other conditions and/or disease states which may appear or occur secondary to the viral infection. These compositions comprise an effective amount of any one or more of the compounds disclosed hereinabove, optionally in combination with a pharmaceutically acceptable additive, carrier or excipient. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound of the instant invention that may be combined with the carrier materials to produce a single dosage form will vary depending upon the host treated, the particular mode of administration. Preferably, the compositions should be formulated so that a dosage of between about 0.01 and 150, preferably about 0.5 to about 25 mg/kg of patient/day of the novel compound can be administered to a patient receiving these compositions.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.25 milligram to about 1 gram, more preferably about 1 milligram to about 750 milligrams, and even more preferably about 10 milligrams to about 500-600 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free compounds or pro-drug forms of the compounds according to the present invention.

In particularly preferred embodiments according to the present invention, the compounds and compositions are used to treat, prevent or delay the onset of viral infections of mammals and in particular HIV 1 and 2 infections in humans. Preferably, to treat, prevent or delay the onset of a viral infection, the compositions will be administered in oral dosage form in amounts ranging from about 250 micrograms up to about 500 mg or more at least once a day, preferably, up to four times a day, within the dosage range used for therapeutic treatment. The present compounds are preferably administered orally, but may be administered parenterally, topically, in suppository or other form.

Certain compounds according to the present invention, because of their low toxicity to host cells, may advantageously be employed prophylactically to prevent (reduce the likelihood of) a viral infection or to prevent the occurrence of clinical symptoms associated with the viral infection, for example AIDS or ARC secondary to HIV. Thus, the present invention also encompasses methods for the prophylactic treatment (preventing, reducing the likelihood or delaying the onset) of viral infections, and in particular HIV and conditions which occur secondary to those viruses. In this aspect according to the present invention, the present compositions are used to prevent reduce the likelihood of or delay the onset of a viral infection, in particular, HIV or a virus related disease or condition such as AIDS or ARC.

This prophylactic method comprises administering to a patient in need of such treatment or who is at risk for the development of an HIV or other viral infection, an amount of a compound according to the present invention effective for alleviating, preventing or delaying the onset of the viral infection or secondary condition or disease state. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (as described hereinabove, as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other anti-viral agents for the treatment of a virus infection as otherwise described herein, especially including other compounds of the present invention or compounds which are otherwise disclosed as being useful for the treatment of HIV, including those presently used to treat HIV such as nucleoside reverse transcriptase inhibitors (NRTI), other non-nucloeoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development, among others as well as compounds which are disclosed in inter alia, U.S. Pat. Nos. 6,240,690; 6,316,505; 6,316,492; 6,232,120; 6,180,604; 6,114,327; 5,891,874; 5,821,242; 5,532,215; 5,491,135; 5,179,084; and 4,880,784, among others, relevant portions of which are incorporated by reference herein.

The compounds disclosed in the above-referenced patents may be used in combination with the present compounds for their additive activity or treatment profile against HIV and/or other viruses and in certain instances, for their synergistic effects in combination with compounds of the present invention. Preferred secondary or additional compounds for use with the present compounds are those which do not inhibit HIV or another virus. Certain compounds according to the present invention may be effective for enhancing the biological activity of certain agents according to the present invention by reducing the metabolism or inactivation of other compounds and as such, are co-administered for this intended effect.

Compounds according to the present invention may be used as active agents in pharmaceutical compositions as inhibitors of reverse transcriptase and as anti-viral agents, said compositions comprising an effective amount of one or more of the compounds disclosed above, formulated as a pharmaceutical dosage form, optionally in combination with a pharmaceutically acceptable carrier, additive or excipient. Pharmaceutical compositions according to the present invention may be used in the treatment of HIV infections (all forms, including human immunodeficiency virus I and II), and numerous additional viral infections, especially including drug resistant forms of these viruses.

In other aspects of the present invention, certain compounds according to the present invention may be used as antagonists in binding assays, as analytical agents, as agents to be used to isolate or purify proteins (especially viral reverse transcriptase), and/or as intermediates in the synthesis of further agents, among other uses.

General Chemistry for Producing Compositions According to the Present Invention

Chemical Synthesis of compounds according to the present invention are generally prepared by cyclizing intermediates to form five-membered heterocyclic rings to which are bonded groups $R^2$—$X^a$ and $R^1$—$X^b$, respectively. The intermediates which are initially prepared or purchased may be readily cyclized to form the various compounds according to the present invention. Various analogous chemical schemes are presented which result in the present compounds.

For example, the oxadiazole derivatives were prepared via cyclization of substituted phenylacetic hydrazides[25] and substituted phenyl isocyanide dichlorides,[26] as illustrated in Scheme 1, FIG. 4 for compound 8. The procedure finds precedent in the synthesis of N,N-diphenyloxadiazol-2,5-diamines from semicarbazides.[27] 1,3,4-Oxadiazole-2-amines were prepared either via cyclization of phenylacetic hydrazides and phenyl isocyanide dichlorides, as described previously (See, Barreiro, et al., *J. Med. Chem.* 2007, 50, 5324-5329), or via cyclization of the hydrazidecarboxamide by heating with $POCl_3$. Representative examples are provided in Schemes 1 and 2 of FIG. 4.

1,3,4-Oxadiazole-2,5-diamines were prepared in a similar manner via a hydrazine-1,2-dicarboxamide intermediate starting from the substituted phenylisocyanates (Scheme 3, FIG. 5). See Gehlen, H.; Moeckel K.; *Liebigs Ann. Chem.*, 1965, 685, 176-180.

Oxazoles were synthesized as shown in Scheme 4, FIG. 5, by minor modification of Froyen's procedure (See, Froyen, P. *Phosphorus, Sulfur Silicon Relat. Elements* 1991, 60, 81-84). Briefly, substituted 2-azidoacetophenones, which are readily obtained from corresponding arylacetic acids, were converted in situ to the iminophosphoranes. Following condensation with various arylisothiocyanates to yield β-keto carbodiimides, the desired oxazoles emerged in good yield.

Compositions which contain alternative groups within the central five-membered heterocyclic ring (thiazole, thiadiazole) may be prepared analogously to the above-described synthetic methods using similar schemes with appropriate literature synthetic support. These are presented in the examples section which appears hereinbelow.

The present invention is now described, purely by way of illustration, in the following examples. It will be understood by one of ordinary skill in the art that these examples are in no way limiting and that variations of detail can be made without departing from the spirit and scope of the present invention.

EXAMPLES

1. General Information

Materials/Methods

NMR spectra were recorded on a Bruker Avance DRX-500 (500 MHz) and DRX-400 (400 MHz) instruments. Column chromatography was carried out employing Merck silica gel (Kieselgel 60, 63-200 μm). Precoated silica gel plates F-254 were used for thin-layer analytical chromatography. HRMS (ESI-TOF) analyses were performed on a 9.4T Bruker Qe FT-ICR MS at the Keck Foundation Biotechnology Resource Laboratory, Yale University.

2. Synthesis of Substituted 1,3,4-Oxadiazoles

Representative Procedure for Preparation of 1,3,4-Oxadiazoles 1 to 5 and 8 to 11

The mixture of 2,6-dichlorophenylacetohydrazide[1] (220 mg, 1.0 mmol), 2,4-dichlorophenyl isocyanide dichloride[1] (0.245 gm, 1.02 mmol), Et$_3$N (3.0 mL, 21.52 mmol) in THF (10.0 mL) was stirred at room temperature for 16 h. After this period, the mixture was filtered through Celite. The filtrate was concentrated under reduced pressure and purified by silica gel chromatography with 20%-50% EtOAc/hexanes to give N-(2,4-dichlorophenyl)-5-(2,6-dichlorobenzyl)-1,3,4-oxadiazol-2-amine (293 mg, 75%).

[1] For the syntheses of substituted phenyl isocyanide dichlorides, see: Van Dort, et al., *J. Med. Chem.* 1987, 30, 1241-1244.

Representative Procedure for Preparation of 1,3,4-Oxadiazole-2-amines 6, 7, 12, 13, 14, 19 and 20

A mixture of 2,6-dichlorophenylacetohydrazide[2] (870 mg, 3.97 mmol) and 4-cyanophenyl isocyanide[3] (580 mg, 4.02 mmol) in dichloromethane (20 mL) was stirred at room temperature for 3 h. The resulting slurry, which became easier to stir after 2 h, was filtered and dried to give a white powder (1.34 g, 92%). The white powder (750 mg, 2.06 mmol) was heated with POCl$_3$[4] (3 mL) under reflux for 2 h. After heating for approximately 1 h, the starting material had dissolved completely. After cooling the mixture it was added to crushed ice (~50 g) and the resulting slurry was neutralized by addition of ammonium hydroxide solution (25% m/V). Filtration and drying gave the crude product as an off-white powder (680 mg) which was purified by silica gel chromatography using 50% EtOAc/hexanes to give N-(4-cyanophenyl)-5-(2,6-dichlorobenzyl)-1,3,4-oxadiazol-2-amine (250 mg, 35%). For the preparation of compounds 19 and 20, the corresponding 2-(2,6-dichlorophenyl)-propanehydrazide was used.

[2] For the syntheses of substituted phenylacetic hydrazides, see: Alanine, et al., *Bioorg. Med. Chem. Lett.* 2004, 14, 817-821.

[3] For compounds 6, 7 and 13 the isocyanates were commercially available, for compound 12 the isocyanate was prepared from the corresponding aniline derivative which was prepared by Zn/acetic acid reduction of the nitro derivative. For preparation of aryl isocyanates see: Brown, et al., *Tetrahedron* 2004, 60, 4361-4375.

[4] In some instances a better yield was achieved by using a mixture of pyridine and POCl$_3$ and prolonged stirring at ambient temperature.

Representative Procedure for Preparation of 1,3,4-Oxadiazole-2,5-diamines 15 and 17

To a cold suspension of hydrazine hydrate (64-65% hydrazine, 1.1 mL, ~22 mmol) in dichloromethane (80 mL) was added 2,6-dichlorophenyl isocyanate (3.76 g, 20.0 mmol) over 30 min. The resulting thick white suspension was stirred at room temperature for 1 h before cooling in an ice-bath. Filtration and drying afforded a white powder (4.29 g, 98%). The semi-carbazide product (1.10 g, 5.0 mmol) was stirred with 4-chlorophenyl isocyanate (770 mg, 5.0 mmol) in dichloromethane (40 mL) at room temperature for 4 h. The resulting slurry, which became easier to stir after 4 h, was filtered and dried to give a white powder (1.79 g, 96%). The hydrazine-1,2-dicarboxamide product (1.00 g, 2.68 mmol) was heated with POCl$_3$ (10 mL) under reflux for 1 h, where after the yellow/brown solution was cooled and added to crushed ice (~50 g) and neutralized by addition of ammonium hydroxide solution (25% m/V). Filtration and drying gave the crude product as an off-white powder (1.07 g) which was purified by silica gel chromatography using 50%-75% EtOAc/hexanes to give N$^2$-(4-chlorophenyl)-N$^5$-(2,6-dichlorophenyl)-1,3,4-oxadiazol-2,5-diamine (0.56 g, 59%).

Procedure for Preparation of N-Methylated 1,3,4-Oxadiazole-2,5-diamine 18

2,6-Dichloroaniline (1.62 g, 10 mmol) in THF (5 mL) was cooled to −78° C. and treated with n-buthyllithium (8 mL of a 1.6 M solution in hexanes). After brief warming to −40° C. the solution was cooled again before addition of iodomethane (0.9 mL, ~15 mmol). The mixture was allowed to warm to room temperature before addition of saturated ammonium chloride solution, extraction with ethyl acetate, drying over anhydrous MgSO$_4$ and solvent evaporation. The resulting residue was purified by column chromatography (dichloromethane) to yield N-methyl-2,6-dichloroaniline (1.70 g, 96%). N-Methyl-2,6-dichloroaniline (0.86 g, 4.89 mmol) dissolved in ethyl acetate (10 mL) was added to an ice-cold solution of phosgene (5.0 mL of a 20% solution in toluene). Cooling was removed and the mixture stirred at room temperature for 10 min and then heated to reflux for 30 min. The solvent was removed and replaced by dichloromethane (20 mL) before drop-wise addition to a cooled (−40° C.) mixture of anhydrous hydrazine (0.64 g, 20 mmol) in dichloromethane (20 mL). The mixture was stirred at room temperature for 2 hours before addition of saturated sodium bicarbonate followed by phase separation and solvent removal to yield N-(2,6-dichlorophenyl)-N-methylhydrazinecarboxamide (1.06 g, 93%).

The N-methylhydrazinecarboxamide product (500 mg, 2.14 mmol) was stirred with 4-chlorophenyl isocyanate (360 mg, 2.48 mmol) in dichloromethane (10 mL) at room temperature for 3 h. The resulting slurry was cooled (−10° C.), filtered, and washed with cold dichloromethane (10 mL) to give a white powder. A third of the product was treated with POCl$_3$ (3 mL) and heated under reflux for 2½ hours, where after the yellow/brown solution was cooled and added to crushed ice (~50 g) and neutralized by addition of ammonium hydroxide solution (25% m/V). Filtration and drying gave the crude product as an off-white powder (280 mg) which was purified by silica gel chromatography using 50%-75% EtOAc/hexanes to give 18 (122 mg, 48%).

Procedure for Preparation of 2-(4-chlorobenzyl)-5-(2,6-dichlorobenzyl)-1,3,4-oxadiazole 16

2,6-Dichlorophenylacetohydrazide[1] (660 mg, 3.01 mmol), 4-chlorophenylacetyl chloride (570 mg, 3.0 mmol) and pyridine (240 µl, 3.00 mmol) were combined in dichloromethane (30 mL) at 0° C. The mixture was stirred for 16 h while warming to room temperature. The mixture was filtered and the recovered white powder dried (0.99 g, 89%). The white powder (700 mg, 1.88 mmol) was heated with POCl$_3$ (10 mL) under reflux for 90 min. After heating for approximately 30 min, the starting material had dissolved completely. After cooling the mixture it was added to crushed ice (~50 g) and the resulting slurry was neutralized by addition of ammonium hydroxide solution (25% m/V). Filtration and drying gave the crude product as an off-white powder (620 mg) which was purified by silica gel chromatography using 50% EtOAc/hexanes to give 2-(4-chlorobenzyl)-5-(2,6-dichlorobenzyl)-1,3,4-oxadiazole (240 mg, 36%).

3. Synthesis of Thiadiazole 21

The mixture of 2,6-dichlorophenylacetic hydrazide[1] (220 mg, 1.0 mmol), 4-chlorophenyl isothiocyanate (169 mg, 1.0 mmol) in ethanol (5 ml) was refluxed for 5 h. After this reaction mixture was concentrated under reduced pressure to get N-(4-chlorophenyl)-2-(2-(2,6-dichlorophenyl)acetyl)hydrazinecarbothioamide in quantitative yield which was used in next step without further purification. N-(4-chlorophenyl)-2-(2-(2,6-dichlorophenyl)acetyl)hydrazinecarbothioamide (380 mg, 0.98 mmol) was added slowly with stirring to ice cold concentrated sulfuric acid (5.0 ml) and the reaction mixture was further stirred in ice bath for 4 h. It was then poured over crushed ice and solid separated was filtered, washed thoroughly with water and recrystallized with methanol to give 21 (300 mg, 78%)[5].

[5]For the syntheses of substituted thiadiazoles, see: Amir, M.; Shikha, K. *Eur. J. Med. Chem.* 2004, 39, 535-545.

4. Synthesis of Substituted Thiazoles

Representative Procedure for Preparation of Thiazoles 22-24[6]

The mixture of 1-chloro-3-(2,6-dichlorophenyl)propan-2-one[7], (237 mg, 1.0 mmol), 1-(4-chlorophenyl)thiourea (244 mg, 1.2 mmol) in ethanol (5 ml) was refluxed for 3 h. After this reaction mixture was concentrated under reduced pressure and crude product was purified by chromatography with basic alumina with 20%-50% EtOAc/hexanes to give N-(4-chlorophenyl)-5-(2,6-dichlorobenzyl)thiazol-2-amine, 22 (240 mg, 65%).

[6]For the syntheses of substituted thiazoles, see: Obushak, N. D.; Matiichuk, V. S.; Vasylyshin, R. Ya.; Ostapyuk, Yu. V. *Russ. J. Org. Chem.* 2004, 40, 383-389.
[7]Kaila, N.; Janz, K.; Huang, A.; Moretto, A.; DeBernardo, S.; Bedard, P. W.; Tam,; Clerin, V.; Keith, J. C. Jr.; Tsao, D. H. H.; Sushkova, N.; Shaw, G. D.; Camphausen, R. T.; Schaub, R. G.; Wang, Q. *J. Med. Chem.* 2007, 50, 40-64.

5. Synthesis of Substituted Oxazoles

Representative Procedure for Preparation of Oxazoles 25-29[8]

The mixture of 1-bromo-3-(2,6-dichlorophenyl)propan-2-one[9], (846 mg, 3 mmol), sodium azide (230 mg, 3.6 mmol) in methanol (10.0 ml) was stirred at room temperature for 90 min. The reaction mixture was concentrated under reduced pressure and the crude product was partitioned between ethyl acetate (50 ml) and water (15 ml). The organic layer was separated, dried over anhydrous sodium sulfate, and concentrated under reduced pressure to give 1-azido-3-(2,6-dichlorophenyl)propan-2-one in quantitative yield.

[8]For the syntheses of substituted oxazoles, see: Harris, P. A.; Cheung, M.; Hunter III, R. N.; Brown, M. L.; Veal, J. M.; Nolte, R. T.; Wang, L.; Liu, W.; Crosby, R. M.; Johnson, J. H.; Epperly, A. H.; Kumar, R.; Luttrell, D. K.; Stafford, J. A. *J. Med. Chem.* 2005, 48, 1610-1619.
[9]Desideri, N. *Lett. Org. Chem.* 2006, 3, 546-548.

To the mixture of 4-fluorophenyl isothiocyanate (153 mg, 1.0 mmol), triphenylphosphine (262 mg, 1.0 mmol) in dichloromethane (3.0 ml) at 0° C. was added solution of 1-azido-3-(2,6-dichlorophenyl)propan-2-one (244 mg, 1.0 mmol) in dichloromethane (4.0 ml). After addition was complete, the ice bath was removed and the mixture was stirred at room temperature for 5 h. Oxalic acid (90 mg, 1 mmol) was added and solid was filtered, washed with dichloromethane and diethyl ether, and partitioned between dichloromethane (20 ml) and 10% aqueous NaOH solution (10 ml). The organic layer was separated and aqueous layer was extracted with additional dichloromethane (2×10 ml). The organic layer was dried over anhydrous sodium sulfate, filtered and concentrated under reduced pressure to get oxazole 26 (260 mg, 77%).

6. $^1$H and $^{13}$C NMR Spectral Data

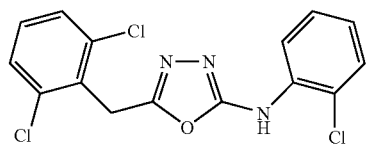

6

$^1$H NMR (500 MHz, CDCl$_3$): δ 8.28 (dd, J=8.3, 1.4 Hz, 1H), 7.37 (d, J=8.1 Hz, 2H), 7.36 (dd, J=8.0, 1.4 Hz, 1H), 7.31 (s, 1H), 7.30 (dt, J=7.9, 1.4 Hz, 1H), 7.22 (t, J=8.1 Hz, 1H), 6.98 (dt, J=7.8, 1.4 Hz, 1H), 4.50 (s, 2H). $^{13}$C NMR (125 MHz, CDCl$_3$): δ 159.3, 157.5, 136.2 (X2), 134.3, 130.3, 129.6, 129.1, 128.5 (X2), 128.2, 123.3, 120.9, 118.4, 27.7. HRMS (ESI-TOF) calcd for C$_{15}$H$_{11}$Cl$_3$N$_3$O [M+H]$^+$ 353.9962. found 353.9957.

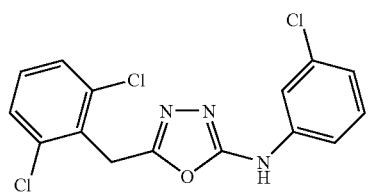

7

$^1$H NMR (500 MHz, CDCl$_3$): δ 9.75 (s, 1H), 7.64 (t, J=2.1 Hz, 1H), 7.42 (ddd, J=8.2, 2.1, 0.7 Hz, 1H), 7.37 (d, J=8.1 Hz 2H), 7.23 (t, J=8.0 Hz, 1H), 7.20 (t, J=8.1 Hz, 1H), 6.94 (ddd, J=8.0, 2.0, 0.7 Hz, 1H), 4.48 (s, 2H). $^{13}$C NMR (125 MHz, CDCl$_3$): δ 160.2, 156.6, 139.9, 136.2 (X2), 134.6, 130.6, 130.0, 129.5, 128.4 (X2), 121.9, 117.3, 115.5, 27.7. HRMS (ESI-TOF) calcd for C$_{15}$H$_{11}$Cl$_3$N$_3$O [M+H]$^+$ 353.9962. found 353.9953.

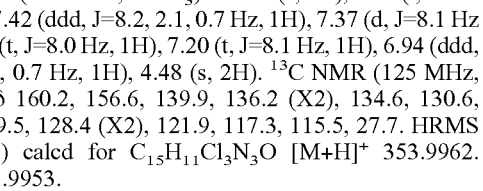

9

$^1$H NMR (400 MHz, DMSO-d$_6$): δ 10.00 (s, 1H), 8.02 (d, J=8.8 Hz, 1H), 7.66 (d, J=2.3 Hz, 1H), 7.57 (d, J=8.1 Hz, 2H), 7.41-7.47 (m, 2H), 4.45 (s, 2H). $^{13}$C NMR (125 MHz, DMSO-d$_6$): δ 160.2, 157.2, 135.2 (X2), 134.5, 130.3, 130.2, 129.0, 128.6 (X2), 127.8, 127.4, 124.4, 122.7, 27.3. HRMS (ESI-TOF) calcd for C$_{15}$H$_{10}$Cl$_4$N$_3$O [M+H]$^+$ 387.9572. found 387.9565.

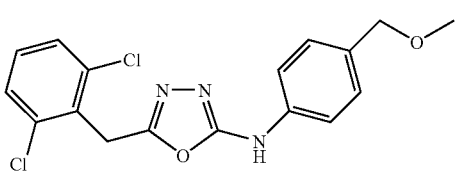

12

$^1$H NMR (500 MHz, CDCl$_3$): δ 7.85 (s, 1H), 7.37 (d, J=8.5 Hz, 2H), 7.35 (d, J=8.1 Hz, 2H), 7.28 (d, J=8.5 Hz, 2H), 7.20

(t, J=8.1 Hz, 1H), 4.49 (s, 2H), 4.40 (s, 2H), 3.36 (s, 3H). $^{13}$C NMR (125 MHz, CDCl$_3$): δ 160.3, 157.0, 137.2, 136.2 (X2), 132.7, 130.4, 129.5, 129.0 (X2), 128.5 (X2), 117.3 (X2), 74.2, 58.0, 27.7. HRMS (ESI-TOF) calcd for C$_{17}$H$_{16}$Cl$_2$N$_3$O$_2$ [M+H]$^+$ 364.0614. found 364.0605.

13

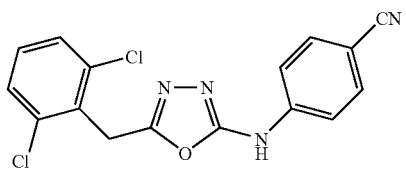

$^1$H NMR (500 MHz, DMSO-d$_6$): δ 11.08 (s, 1H), 7.81 (d, J=8.8 Hz, 2H), 7.70 (d, J=8.8 Hz, 2H), 7.58 (d, J=9.5 Hz, 2H), 7.43 (t, J=9.5 Hz, 1H), 4.49 (s, 2H). $^{13}$C NMR (125 MHz, DMSO-d$_6$): δ 159.6, 157.4, 143.1, 135.7 (X2), 133.9 (X2), 130.7, 129.1 (X2), 119.6, 117.5 (X2), 103.7, 27.7. HRMS (ESI-TOF) calcd for C$_{16}$H$_{11}$Cl$_2$N$_4$O [M+H]$^+$ 345.0304. found 345.0299.

14

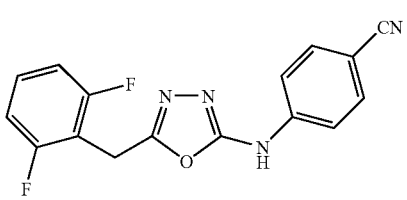

$^1$H NMR (500 MHz, DMSO-d$_6$): δ 11.06 (s, 1H), 7.79 (d, J=8.8 Hz, 2H), 7.70 (d, J=8.8 Hz, 2H), 7.47 (m, 1H), 7.17 (m, 2H), 4.26 (s, 2H). $^{13}$C NMR (125 MHz, DMSO-d$_6$): δ 161.2 (d, J=246 Hz) (X2), 159.6, 157.8, 143.1, 133.9 (X2), 130.6 (t, J=10.3 Hz), 119.5, 117.5 (X2), 112.1 (dd, J=19.8, 5.3 Hz) (X2), 110.6 (t, J=19.7 Hz), 103.7, 18.8. HRMS (ESI-TOF) calcd for C$_{16}$H$_{10}$F$_2$N$_4$O [M+H]$^+$ 313.0895. found 313.0889.

15

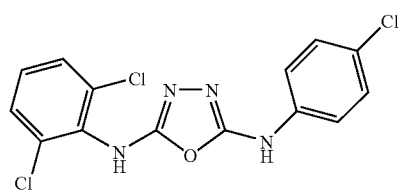

$^1$H NMR (500 MHz, DMSO-d$_6$): δ 10.11 (s, 2H), 7.53 (d, J=8.3 Hz, 2H), 7.49 (d, J=9.1 Hz, 2H), 7.35 (d, J=9.1 Hz, 2H), 7.26 (t, J=8.3 Hz, 1H). $^{13}$C NMR (125 MHz, DMSO-d$_6$): δ 154.8, 154.2, 138.4, 136.0, 132.3, 129.2 (X2), 129.1 (X2), 127.7, 125.4, 118.6 (X2). HRMS (ESI-TOF) calcd for C$_{14}$H$_9$Cl$_3$N$_4$O [M+H]$^+$ 354.9915. found 354.9907.

16

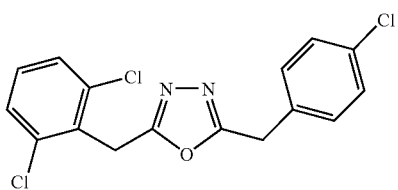

$^1$H NMR (500 MHz, DMSO-d$_6$): δ 7.49 (d, J=8.2 Hz, 2H), 7.36 (d, J=8.8 Hz, 2H), 7.35 (t, J=8.2 Hz, 1H), 7.28 (d, J=8.8 Hz, 2H), 4.42 (s, 2H), 4.22 (s, 2H). $^{13}$C NMR (125 MHz, DMSO-d$_6$): δ 165.3, 163.4, 135.1 (X2), 133.3, 131.9, 130.7 (X3), 130.3, 128.6 (X2), 128.6 (X2), 29.8, 27.3. HRMS (ESI-TOF) calcd for C$_{16}$H$_{11}$Cl$_3$N$_2$O [M+H]$^+$ 353.0010. found 352.9997.

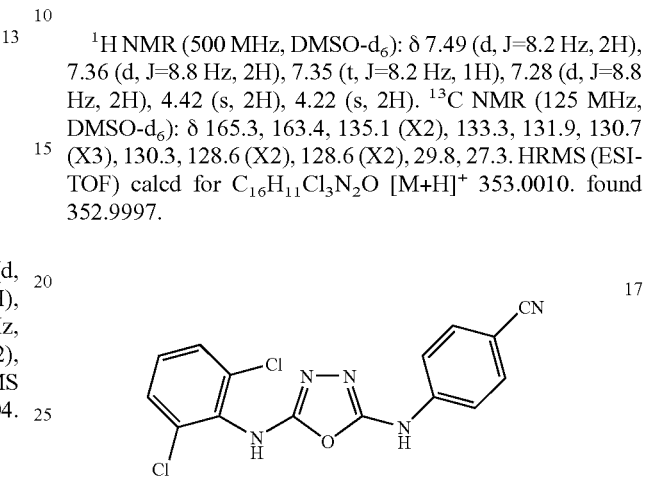

17

$^1$H NMR (500 MHz, DMSO-d$_6$): δ 10.79 (s, 1H), 10.1 (br S, 1H), 7.77 (d, J=8.8 Hz, 2H), 7.62 (d, J=8.8 Hz, 2H), 7.55 (d, J=8.1 Hz, 2H), 7.29 (t, J=8.1 Hz, 1H). $^{13}$C NMR (125 MHz, DMSO-d$_6$): δ 156, 153.8, 143.3, 133.8 (X2), 132.6 (X2), 129.3 (X2), 128.9, 128.3, 119.7, 117.1 (X2), 103.2. HRMS (ESI-TOF) calcd for C$_{15}$H$_9$Cl$_2$N$_5$O [M+H]$^+$ 346.0257. found 346.0253.

18

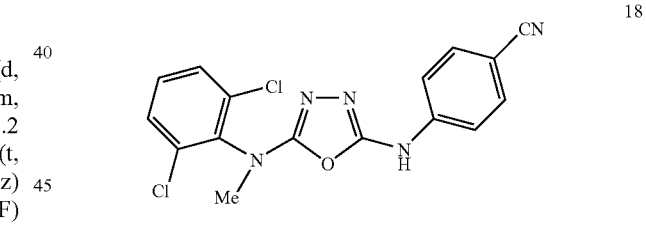

$^1$H NMR (500 MHz, DMSO-d$_6$): δ 10.71 (s, 1H), 7.71 (d, J=8.8 Hz, 2H), 7.63 (d, J=8.1 Hz, 2H), 7.55 (d, J=8.8 Hz, 2H), 7.44 (t, J=8.1 Hz, 1H), 3.27 (s, 3H). $^{13}$C NMR (125 MHz, DMSO-d$_o$): δ 157.0, 154.3, 142.8, 136.5, 134.5 (X2), 133.4 (X2), 130.9, 129.5 (X2), 119.2, 116.6 (X2), 102.7, 36.9. HRMS (ESI-TOF) calcd for C$_{16}$H$_{11}$Cl$_2$N$_5$O [M+H]$^+$ 360.0413. found 360.0402.

19

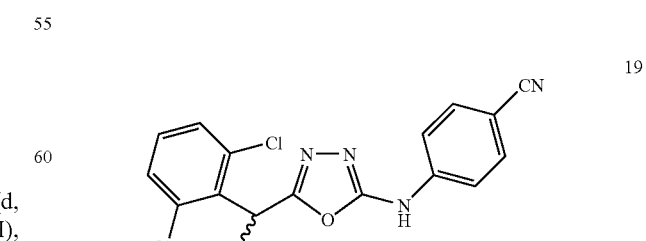

$^1$H NMR (500 MHz, DMSO-d$_6$): δ 10.99 (s, 1H), 7.75 (d, J=8.7 Hz, 2H), 7.63 (d, J=8.7 Hz, 2H), 7.48 (d, J=8.1 Hz, 2H), 7.36 (t, J=8.1 Hz, 1H), 5.07 (q, 1H), 1.68 (d, J=7.1 Hz, 3H). $^{13}$C NMR (125 MHz, DMSO-d$_6$): δ 160.8, 158.9, 142.7, 135.3, 134.2 (X), 133.5 (X), 130.2 (X), 129.6, 119.1, 116.9 (X), 103.2, 33.4, 14.5. HRMS (ESI-TOF) calcd for C$_{17}$H$_{12}$Cl$_2$N$_4$O [M+H]$^+$ 359.0461. found 359.0456.

20

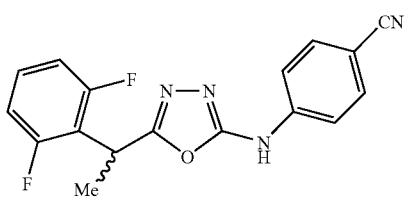

$^1$H NMR (500 MHz, Acetone-d$_6$): δ 9.84 (s, 1H), 7.85 (d, J=9.0 Hz, 2H), 7.75 (d, J=9.0 Hz, 2H), 7.44 (m, 1H), 7.07 (m, 2H), 4.73 (q, J=7.2 Hz, 1H), 1.78 (d, J=7.2 Hz, 3H). $^{13}$C NMR (125 MHz, Acetone-d$_6$): δ 161.6, 161.4 (d, J=253 Hz) (X2), 159.8, 143.2, 133.8 (X2), 130.3 (t, J=10.5 Hz), 119.1, 117.7 (X2), 116.8 (t, J=17.4 Hz), 112.3 (dd, J=20.7, 5.1 Hz) (X2), 105.0, 27.1, 16.5. HRMS (ESI-TOF) calcd for C$_{17}$H$_{12}$F$_2$N$_4$O [M+H]$^+$ 327.1052. found 327.1044.

21

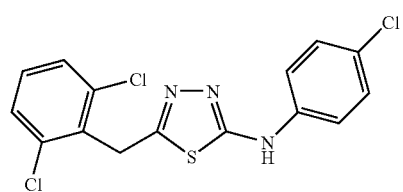

$^1$H NMR (500 MHz, DMSO-d$_6$): δ 10.40 (s, 1H), 7.60 (d, J=8.8 Hz, 2H), 7.55 (d, J=8.2 Hz, 2H), 7.41 (d, J=7.9 Hz, 1H), 7.37 (d, J=9.1 Hz, 2H), 4.55 (s, 2H). $^{13}$C NMR (125 MHz, DMSO-d$_6$): δ 156.0, 139.8, 135.4, 133.5, 130.5, 129.2 (X2), 129.1 (X2), 125.6, 119.2 (X2), 119.1, 31.9. FIRMS (ESI-TOF) calcd for C$_{15}$H$_{11}$Cl$_3$N$_3$S [M+H]$^+$ 371.9705. found 371.9691.

22

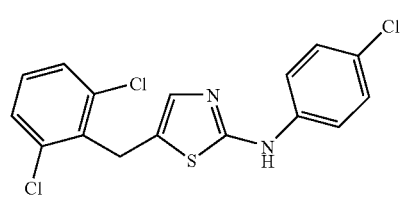

$^1$H NMR (500 MHz, CDCl$_3$): δ 7.18-7.24 (m, 7H), 7.06-7.10 (m, 1H), 5.90 (s, 1H), 4.23 (s, 2H). $^{13}$C NMR (125 MHz, CDCl$_3$): δ 164.6, 149.0, 139.3, 136.5, 135.2, 129.8 (X2), 128.9, 128.7 (X2), 128.2, 119.8 (X2), 103.4, 33.9. HRMS (ESI-TOF) calcd for C$_{16}$H$_{12}$Cl$_3$N$_2$S [M+H]$^+$ 370.9752. found 370.9748.

23

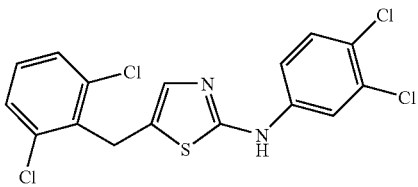

$^1$H NMR (500 MHz, CDCl$_3$): δ 7.59 (s, 1H), 7.23-7.27 (m, 3H), 7.05-7.09 (m, 2H), 5.98 (s, 1H), 4.22 (s, 2H). $^{13}$C NMR (125 MHz, CDCl$_3$): δ 163.8, 148.9, 140.1, 136.5, 135.0, 133.5, 131.1, 128.9, 128.7 (X2), 126.0, 119.8, 117.6, 104.1, 33.8. HRMS (ESI-TOF) calcd for C$_{16}$H$_{11}$Cl$_4$N$_2$S [M+H]$^+$ 404.9362. found 404.9355.

24

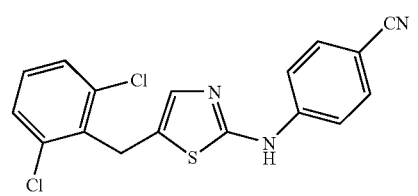

$^1$H NMR (500 MHz, DMSO-d$_6$): δ 10.66 (s, 1H), 7.74 (d, J=8.8 Hz, 2H), 7.65 (d, J=8.8 Hz, 2H), 7.47 (d, J=8.2 Hz, 2H), 7.30 (t, J=8.2 Hz, 1H), 6.41 (s, 1H), 4.20 (s, 2H). $^{13}$C NMR (125 MHz, DMSO-d$_6$): δ 161.8, 147.9, 144.8, 135.1, 134.4, 133.2 (X2), 129.2, 128.4 (X2), 119.4, 116.5 (X2), 104.9, 101.9, 33.0. HRMS (ESI-TOF) calcd for C$_{17}$H$_{12}$Cl$_2$N$_3$S [M+H]$^+$ 360.0123. found 360.0117.

25

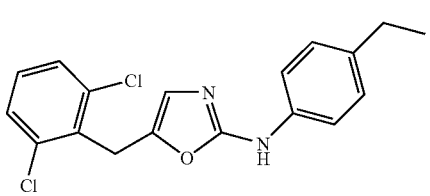

$^1$H NMR (500 MHz, DMSO-d$_6$): δ 9.77 (s, 1H), 7.46-7.49 (m, 2H), 7.39-7.41 (m, 2H), 7.30-7.32 (m, 1H), 7.03-7.05 (m, 2H), 6.51 (bs, 1H), 4.17 (s, 2H), 2.46 (m, 2H), 1.10 (m, 3H). $^{13}$C NMR (125 MHz, DMSO-d$_6$): δ 156.0, 140.2, 137.3, 136.0, 134.9, 132.6, 129.6, 128.7 (X2), 127.9 (X2), 122.7, 116.3 (X2), 27.4, 27.1, 15.7. HRMS (ESI-TOF) calcd for C$_{18}$H$_{17}$Cl$_2$N$_2$O [M+H]$^+$ 347.0712. found 347.0709.

26

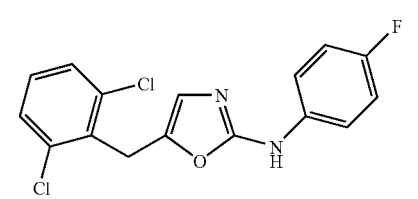

$^1$H NMR (500 MHz, DMSO-d$_6$): δ 9.69 (s, 1H), 7.26-7.28 (m, 2H), 7.22-7.24 (m, 2H), 7.06-7.09 (m, 1H) 6.79-6.82 (m, 2H), 6.29 (s, 1H), 3.94 (s, 2H). $^{13}$C NMR (125 MHz, DMSO-d$_6$): δ 155.9, 140.4, 135.9, 134.9, 132.5, 129.6, 128.7 (X2), 122.6, 117.7, 117.6, 115.3, 115.1, 27.0. HRMS (ESI-TOF) calcd for $C_{16}H_{12}Cl_2FN_2O$ [M+H]$^+$ 337.0305. found 337.0300.

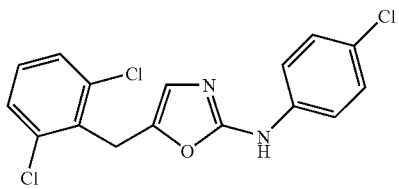

27

$^1$H NMR (500 MHz, DMSO-d$_6$): δ 10.21 (s, 1H), 7.63-7.66 (m, 2H), 7.57-7.60 (m, 2H), 7.41-7.44 (m, 1H), 7.36-7.40 (m, 2H), 6.67 (s, 1H), 4.30 (s, 2H). $^{13}$C NMR (125 MHz, DMSO-d$_6$): δ 155.5, 140.7, 138.4, 134.9, 132.4, 129.7, 128.7 (X2), 128.5 (X2), 124.3, 122.6, 117.8 (X2), 27.0. HRMS (ESI-TOF) calcd for $C_{16}H_{12}Cl_3N_2O$ [M+H]$^+$ 353.0009. found 353.0006.

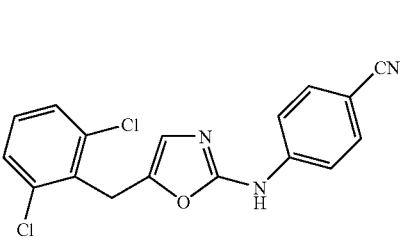

28

$^1$H NMR (500 MHz, DMSO-d$_6$): δ 10.06 (s, 1H), 7.67 (bs, 4H), 7.47 (d, J=7.2 Hz, 2H), 7.31 (t, J=7.8 Hz, 1H), 6.64 (s, 1H), 4.21 (s, 2H). $^{13}$C NMR (125 MHz, DMSO-d$_6$): δ 154.7, 143.4, 141.4, 134.9, 133.3 (X2), 132.3, 129.7, 128.7 (X2), 122.9, 119.4, 116.3 (X2), 102.1, 27.0. HRMS (ESI-TOF) calcd for $C_{17}H_{12}Cl_2N_3O$ [M+H]$^+$ 344.0351. found 344.0348.

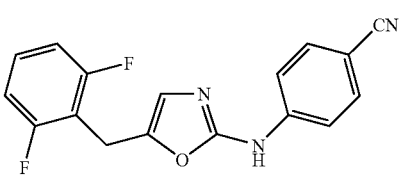

29

$^1$H NMR (500 MHz, DMSO-d$_6$): δ 10.70 (s, 1H), 7.72-7.76 (m, 4H), 7.45 (t, J=7.9 Hz, 1H), 7.16-7.20 (m, 2H), 6.80 (s, 1H), 4.08 (s, 2H). $^{13}$C NMR (125 MHz, DMSO-d$_6$): δ 160.6 (dd, J=241 Hz, 8.3 Hz), 154.8, 143.5, 142.2, 133.3 (X2), 129.5 (t, J=10.1 Hz), 122.2, 119.4, 116.3 (X2), 112.6 (t, J=20.2 Hz), 111.6 (dd, J=20.2 Hz, 5.5 Hz), 102.1, 18.0 (t, J=3.7 Hz). HRMS (ESI-TOF) calcd for $C_{17}H_{12}F_2N_3O$ [M+H]$^+$ 312.0942. found 312.0934.

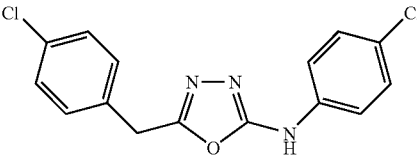

11

11 JL0195 $^1$H NMR (500 MHz, DMSO-d$_6$): δ 10.53 (s, 1H), 7.50 (d, J=8.8 Hz, 2H), 7.38 (d, J=8.3 Hz, 2H), 7.34 (d, J=8.3 Hz, 2H), 7.32 (d, J=8.8 Hz, 2H), 4.16 (s, 2H). $^{13}$C NMR (125 MHz, DMSO-d$_6$): δ 159.7, 158.5, 137.6, 133.8, 131.8, 130.7 (X2), 128.8 (X2), 128.6 (X2), 125.2, 118.3 (X2), 29.9. LRMS (ESI-TOF) calcd for $C_{15}H_{12}Cl_2N_3O$ [M+1]$^+$ 320. found 320.1. HRMS (ESI-TOF) calcd for $C_{15}H_{12}Cl_2N_3O$ [M+1]$^+$ 320.0357. found 320.0364.

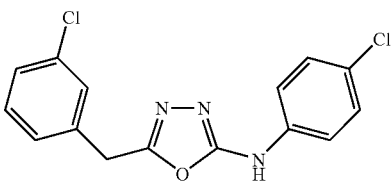

12

12 JL0196 $^1$H NMR (500 MHz, DMSO-d$_6$): δ 10.06 (s, 1H), 7.52 (d, J=8.8 Hz, 2H), 7.40 (s, 1H), 7.36-7.31 (m, 1H), 7.34 (d, J=6.9 Hz, 1H), 7.33 (d, J=8.8 Hz, 2H), 7.26 (d, J=6.9 Hz, 1H), 4.24 (s, 2H). $^{13}$C NMR (125 MHz, DMSO-d$_6$): δ 159.7, 158.3, 137.6, 137.1, 133.2, 130.5, 128.8, 128.7 (X2), 127.6, 127.1, 125.2, 118.3 (X2), 30.1. LRMS (ESI-TOF) calcd for $C_{15}H_{12}Cl_2N_3O$ [M+1]$^+$ 320. found 320.1. HRMS (ESI-TOF) calcd for $C_{15}H_{12}Cl_2N_3O$ [M+1]$^+$ 320.0357. found 320.0363.

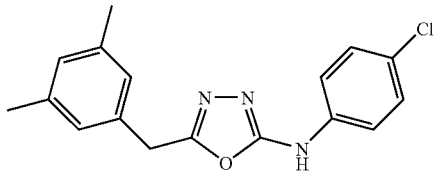

13

13 JL0197 $^1$H NMR (500 MHz, DMSO-d$_6$): δ 10.50 (s, 1H), 7.51 (d, J=8.8 Hz, 2H), 7.33 (d, J=8.8 Hz, 2H), 6.87 (s, 3H), 4.03 (s, 2H), 2.20 (s, 6H). $^{13}$C NMR (125 MHz, DMSO-d$_6$): δ 159.6, 158.9, 137.7 (X2), 137.6, 134.5, 128.8 (X2), 128.5 (X2), 126.4, 125.1, 118.3 (X2), 30.5, 20.7 (X2). LRMS (ESI-TOF) calcd for $C_{17}H_{17}ClN_3O$ [M+1]$^+$ 314. found 314.1. HRMS (ESI-TOF) calcd for $C_{17}H_{17}ClN_3O$ [M+1]$^+$ 314.1060. found 314.1059.

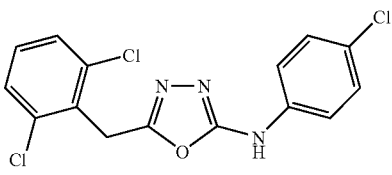

14

14 JL0198 $^1$H NMR (500 MHz, DMSO-d$_6$): δ 10.58 (s, 1H), 7.57-7.54 (m, 4H), 7.43-7.37 (m, 3H), 4.45 (s, 2H). $^{13}$C NMR (125 MHz, DMSO-d$_6$): δ 160.0, 156.8, 138.0, 135.7, 130.9, 130.7, 129.2 (X2), 129.1 (X2), 125.7, 118.8 (X2), 27.7. LRMS (ESI-TOF) calcd for $C_{15}H_{11}Cl_3N_3O$ [M+1]$^+$ 354. found 354.0. HRMS (ESI-TOF) calcd for $C_{15}H_{11}Cl_3N_3O$ [M+1]$^+$ 353.9968. found 353.9955.

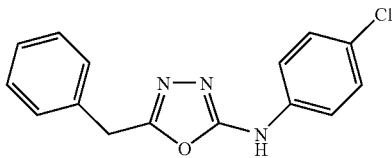

15

15 JL0199 $^1$H NMR (500 MHz, DMSO-d$_6$): δ 10.58 (s, 1H), 7.59 (d, J=7.8 Hz, 2H), 7.42-7.31 (m, 7H), 4.21 (s, 2H). $^{13}$C NMR (125 MHz, DMSO-d$_6$): δ 160.1, 159.3, 138.1, 135.2, 129.2 (X2), 129.1 (X2), 129.0 (X2), 127.5, 125.6, 118.8 (X2), 31.1. LRMS (ESI-TOF) calcd for C$_{15}$H$_{13}$ClN$_3$O [M+1]$^+$ 286. found 286.1. HRMS (ESI-TOF) calcd for C$_{15}$H$_{13}$ClN$_3$O [M+1]$^+$ 286.0747. found 286.0753.

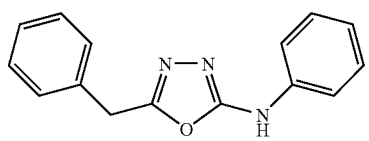

16

16 JL0200 $^1$H NMR (500 MHz, DMSO-d$_6$): δ 10.33 (s, 1H), 7.49 (d, J=7.5 Hz, 2H), 7.34-7.23 (m, 7H), 6.93 (t, J=7.3 Hz, 1H), 4.13 (s, 2H). $^{13}$C NMR (125 MHz, DMSO-d$_6$): δ 159.9, 158.6, 138.6, 134.8, 128.9 (X2), 128.7 (X2), 128.6 (X2), 127.0, 121.5, 116.7 (X2), 30.6. LRMS (ESI-TOF) calcd for C$_{15}$H$_{14}$N$_3$O [M+1]$^+$ 252. found 252.1. HRMS (ESI-TOF) calcd for C$_{15}$H$_{14}$N$_3$O [M+1]$^+$ 252.1137. found 252.1131.

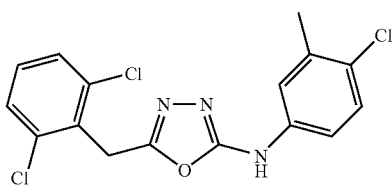

17

17 JL0201 $^1$H NMR (500 MHz, DMSO-d$_6$): δ 10.48 (s, 1H), 7.52 (d, J=7.8 Hz, 2H), 7.44 (d, J=2.4 Hz, 1H), 7.37 (dd, J=8.0, 0.5 Hz, 1H), 7.32 (d, J=2.4 Hz, 1H), 7.31 (s, 1H), 4.40 (s, 2H), 2.25 (s, 3H). $^{13}$C NMR (125 MHz, DMSO-d$_6$): δ 159.6, 156.3, 137.6, 135.8, 135.2 (X2), 130.4, 130.3, 129.2, 128.7 (X2), 125.6, 119.1, 116.1, 27.2, 19.9. LRMS (ESI-TOF) calcd for C$_{16}$H$_{13}$Cl$_3$N$_3$O [M+1]$^+$ 368. found 368.0. HRMS (ESI-TOF) calcd for C$_{16}$H$_{13}$Cl$_3$N$_3$O [M+1]$^+$ 368.0124. found 368.0122.

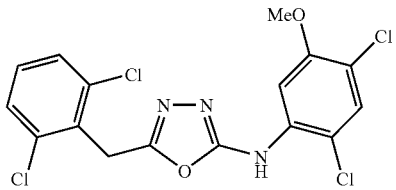

18

18 JL0202 $^1$H NMR (500 MHz, DMSO-d$_6$): δ 10.00 (s, 1H), 7.87 (s, 1H), 7.54 (d, J=7.8 Hz, 2H), 7.40 (t, J=7.8 Hz, 1H), 4.43 (s, 2H), 3.82 (s, 3H). $^{13}$C NMR (125 MHz, DMSO-d$_6$): δ 160.1, 157.2, 153.7 (X2), 135.2 (X2), 130.3, 130.2, 129.7, 128.6 (X2), 115.3, 114.3, 105.6, 56.3, 27.3. LRMS (ESI-TOF) calcd for C$_{16}$H$_{12}$Cl$_4$N$_3$O$_2$ [M+1]$^+$ 420. found 420.0. HRMS (ESI-TOF) calcd for C$_{16}$H$_{12}$Cl$_4$N$_3$O$_2$ [M+1]$^+$ 417.9684. found 417.9695.

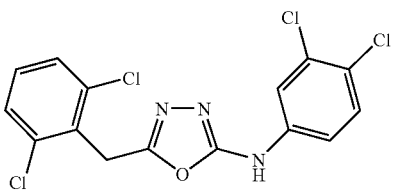

19

19 JL0203 $^1$H NMR (500 MHz, DMSO-d$_6$): δ 10.79 (s, 1H), 7.80 (d, J=2.6 Hz, 1H), 7.54 (s, 1H), 7.51 (d, J=7.8 Hz, 2H), 7.40 (d, J=2.6 Hz, 1H), 7.38 (t, J=7.8 Hz, 1H), 4.41 (s, 2H). $^{13}$C NMR (125 MHz, DMSO-d$_6$): δ 159.2, 156.6, 138.7, 135.2 (X2), 131.2, 130.9, 130.3, 130.2, 128.7 (X2), 123.1, 118.0, 117.2, 27.2. LRMS (ESI-TOF) calcd for C$_{15}$H$_{10}$Cl$_4$N$_3$O [M+1]$^+$ 390. found 390.0. HRMS (ESI-TOF) calcd for C$_{15}$H$_{10}$Cl$_4$N$_3$O [M+1]$^+$ 387.9578. found 387.9594.

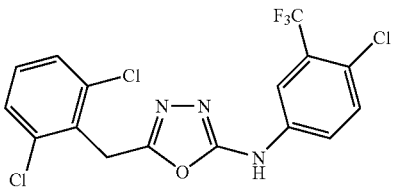

20

20 JL0204 $^1$H NMR (500 MHz, DMSO-d$_6$): δ 10.98 (s, 1H), 8.10 (d, J=2.3 Hz, 1H), 7.76 (dd, J=8.8, 2.3 Hz, 1H), 7.68 (d, J=8.8 Hz, 1H), 7.57 (d, J=8.1, 2H), 7.42 (t, J=8.1 Hz, 1H), 4.47 (s, 2H). $^{13}$C NMR (125 MHz, DMSO-d$_6$): δ 159.2, 156.7, 138.1, 135.2 (X2), 132.3, 130.3 (X2), 128.7 (X2), 126.7 (q, J=31.0 Hz), 122.6 (q, J=273.1 Hz), 122.2, 121.7, 115.5 (q, J=5.4 Hz), 27.2. $^{19}$F NMR (376 MHz, DMSO-d$_6$): δ-61.6. LRMS (ESI-TOF) calcd for C$_{16}$H$_{10}$Cl$_3$F$_3$N$_3$O [M+1]$^+$ 422. found 422.0. FIRMS (ESI-TOF) calcd for C$_{16}$H$_{10}$Cl$_3$F$_3$N$_3$O [M+1]$^+$ 421.9842. found 421.9847.

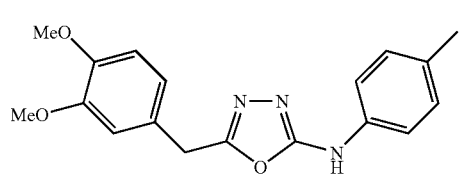

1

(S10087)

$^1$H NMR (500 MHz, DMSO-d$_6$): δ 10.15 (s, 1H), 7.36 (d, J=8.5 Hz, 2H), 7.07 (d, J=8.5 Hz, 2H), 6.89 (d, J=1.9 Hz, 1H), 6.88 (d, J=8.0 Hz, 1H), 6.78 (dd, J=8.2, 1.9 Hz, 1H), 4.03 (s, 2H), 3.70 (s, 3H), 3.69 (s, 3H), 2.20 (s, 3H). LRMS (ESI-TOF) calcd for C$_{18}$H$_{20}$N$_3$O$_3$ [M+1]$^+$ 326. found 326.1.

Biological Activity

The primary assay determined activities against the wild-type strain IIIB of HIV-1 (See, Popovic, et al., *Lancet*, 1984, 2, 1472-1473; Popovic, et al., *Science*, 1984, 224, 497-500; Ratner, L., *Nature*, 1985, 313, 277-284) by use of MT-2 human T-cells (See, Haertle, et al., *J. Biol. Chem.*, 1988, 263, 5870-5875 and Harada, et al., *Science*, 1985, 229, 563-566) at a multiplicity of infection (MOI) of 0.1. $EC_{50}$ values are obtained as the dose required to achieve 50% 50% protection of the infected cells by the MTT colorimetric method. $CC_{50}$ for inhibition of MT-2 cell growth by 50% is obtained simultaneously. See, Lin, et al., *Biochem. Pharmacol.*, 1994, 47, 171-174 and Ray, et al., *Antimicob. Agents Chemother.*, 2002, 46, 887-891. Analogous assays were performed (where indicated) with variant strains of the virus that encode the Tyr181Cys (Y181C) and Lys103Asn/Y181C (K103N/Y181C) mutant forms of HIV-RT.

FIGS. 3-10 and 12-13, in tables 1-10, display the results of biological testing of a number of compounds according to the present invention. In general, compounds according to the present invention show anti-HIV active in the µM range (lower numbers are more potent) and are generally, relatively non-toxic (larger number evidences lower toxicity).

A number of additional embodiments of various compounds according to the present invention are set forth in attached FIGS. 13-16.

The terms and expressions that have been employed in this application are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

REFERENCES 1) 2006 *AIDS Epidemic Update*: UNAIDS: Geneva, 2006.
2) (a) Kohlstaedt, L. A.; Wang, J.; Friedman, J. M.; Rice, P. A.; Steitz, T. A. *Science* 1992, 256, 1783-1790. (b) Smerdon, S. J.; Jager, J.; Wang, J.; Kohlstaedt, L. A.; Chirino, A. J.; Friedman, J. M.; Rice, P. A.; Steitz, T. A. *Proc. Natl. Acad. Sci. U.S.A.* 1994, 91, 3911-3915. (c) De Clercq, E. J. *Med. Chem.* 2005, 48, 1297-313.
3) (a) Jorgensen, W. L.; Ruiz-Caro, J.; Tirado-Rives, J.; Basavapathruni, A.; Anderson, K. S.; Hamilton, A. D. *Bioorg. Med. Chem. Lett.* 2006, 16, 663-667. (b) Ruiz-Caro, J.; Basavapathruni, A.; Kim, J. T.; Wang, L.; Bailey, C. M.; Anderson, K. S.; Hamilton, A. D.; Jorgensen, W. L. *Bioorg. Med. Chem. Lett.* 2006. 16, 668-671. (c) Thakur, V. V.; Kim, J. T.; Hamilton, A. D.; Bailey, C. M.; Domaoal, R. A.; Wang, L.; Anderson, K. S.; Jorgensen, W. L. *Bioorg. Med. Chem. Lett.* 2006, 16, 5664-5667. (d) Kim, J. T.; Hamilton, A. D.; Bailey, C. M.; Domaoal, R. A.; Wang, L.; Anderson, K. S.; Jorgensen, W. L. *J. Am. Chem. Soc.* 2006, 128, 15372-15373.
4) (a) Blake, J. F.; Laird, E. R. *Ann. Rep. Med. Chem.* 2003, 38, 305-314. (b) Leach, A. R.; Shoichet, B. K.; Peishoff, C. E. *J. Med. Chem.* 2006, 49, 5851-5855.
5) Barreiro, G.; Guimaraes, C. R. W.; Tubert-Brohman, I.; Tirado-Rives, J.; Jorgensen, W. L., *J. Chem. Info. Model.*, submitted.
6) Ren, J.; Esnouf, R. M.; Hopkins, A. L.; Warren, J.; Balzarini, J.; Stuart, D. I.; Stammers, D. K. Crystal structures of HIV-1 reverse transcriptase in complex with carboxanilide derivatives. *Biochemistry* 1998, 37, 14394-14403.
7) Friesner, R. A.; Banks, J. L.; Murphy, R. B.; Halgren, T. A.; Klicic, J. J.; Mainz, D. T.; Repasky, M. P.; Knoll, E. H.; Shelley, M.; Perry, J. K.; Shaw, D. E.; Francis, P.; Shenkin, P. S. *J. Med. Chem.* 2004, 47, 1739-1749.
8) (a) Jorgensen, W. L.; Maxwell, D. S.; Tirado-Rives, J. *J. Am. Chem. Soc.* 1996, 118, 11225-11236. (b) Jorgensen, W. L.; Tirado-Rives, *J. Proc. Nat. Acad. Sci. USA* 2005, 102, 6665-6670.
7) (a) Still, W. C.; Tempczyk, A.; Hawley, R. C.; Hendrickson, T. *J. Am. Chem. Soc.* 1990, 112, 6127-6129. (b) Jorgensen, W. L.; Ulmschneider, J. P.; Tirado-Rives, J. *J. Phys. Chem. B* 2004, 108, 16264-16270.
8) MacroModel, version 9.0, Schrodinger LLC, New York, N.Y., 2005.
9) (a) Lin, T. S.; Luo, M. Z.; Liu, M. C.; Pai, S. B.; Dutschman, G. E.; Cheng, Y. C. *Biochem. Pharmacol.* 1994, 47, 171-174. (b) Ray, A. S.; Yang, Z.; Chu, C. K.; Anderson, K. S. *Antimicrob. Agents Chemother.* 2002, 46, 887-891.
10) (a) Muraglia, E.; Kinzel, O. D.; Laufer, R.; Miller, M. D.; Moyer, G.; Munshi, V.; Orvieto, F.; Palumbi, M. C.; Pescatore, G.; Rowley, M.; Williams, P. D.; Summa, V. *Bioorg. Med. Chem. Lett.* 2006, 16, 2748-2752. (b) Wang, Z.; Wu, B.; Kuhen, K. L.; Bursulaya, B.; Nguyen, T. N.; Nguyen, D. G.; He, Y. *Bioorg. Med. Chem. Lett.* 2006, 16, 4174-4177. (c) De La Rosa, M.; Kim, H. W.; Gunic, E.; Jenket, C.; Boyle, U.; Koh, Y.-H.; Korboukh, I.; Allan, M.; Zhang, W.; Chen, H.; Xu, W.; Nilar, S.; Yao, N.; Hamatake, R.; Lang, S. A.; Hong, Z.; Zhang, Z. & Girardet, J.-L. *Bioorg. Med. Chem. Lett.* 2006, 16, 4444-4449.
11) Tirado-Rives, J.; Jorgensen, W. L. *J. Med. Chem.* 2006, 49, 5880-5884.
14) Hann, M. M.; Leach, A. R.; Harper, G. J. *Chem. Inf. Comput. Sci.* 2001, 41, 856-864.
15) Rizzo, R. C.; Udier-Blagovic, M.; Wang, D. P.; Watkins, E. K.; Kroeger Smith, M. B.; Smith, Jr., R. H.; Tirado-Rives, J.; Jorgensen, W. L. *J. Med. Chem.* 2002, 45, 2970-2987.
16) Blagovic, M. U.; Tirado-Rives, J.; Jorgensen, W. L. *J. Am. Chem. Soc.* 2003, 125, 6016-6017.
17) Das, K.; Clark, A. D., Jr.; Lewi, P. J.; Heeres, J.; de Jonge, M. R.; Koymans, L. M. H.; Vinkers, H. M.; Daeyaert, F.; Ludovici, D. W.; Kukla, M. J.; De Corte, B.; Kavash, R. W.; Ho, C. Y.; Ye, H.; Lichtenstein, M. A.; Andries, K.; Pauwels, R.; de Bethune, M.-P.; Boyer, P. L.; Clark, P.; Hughes, S. H.; Janssen, P. A. J.; Arnold, E. *J. Med. Chem.* 2004, 47, 2550-2560.
18) Pyrimidines such as JL0092 are in the class Het-NH-Ph-U in which the U group is now delivered into the aryl box formed by Tyr181, Tyr188, Trp229, and Phe227 from the "right" instead of from the "left" as in FIG. 1 for 510087.
19) Ludovici, D. W.; De Corte, B. L.; Kukla, M. J.; Ye, H.; Ho, C. Y.; Lichtenstein, M. A.; Kavash, R. W.; Andries, K.; de Bethune, M.-P.; Azijn, H.; Pauwels, R.; Lewi, P. J.; Heeres, J.; Koymans, L. M. H.; de Jonge, M. R.; Van Aken, K. J. A.;

Daeyaert, F. F. D.; Das, K.; Arnold, E.; Janssen, P. A. *J. Moorg. Med. Chem. Lett.* 2001, 11, 2235-2239.
20) Heeres, J.; de Jonge, M. R.; Koymans, L. M. H.; Daeyaert, F. F. D.; Vinkers, M.; Van Aken Koen, J. A.; Arnold, E.; Das, K.; Kilonda, A.; Hoornaert, G. J.; Compernolle, F.; Cegla, M.; Azzam, R. A.; Andries, K.; de Bethune, M.-P.; Azijn, H.; Pauwels, R.; Lewi, P. J.; Janssen, P. A J *J. Med. Chem.* 2005, 48, 1910-8.
21) QikProp, v 3.0; Schrodinger LLC: New York, 2006. QikProp is called as a subroutine by BOMB for each generated structure.
22) Himmel, D. M.; Das, K.; Clark, A. D., Jr.; Hughes, S. H.; Benjahad, A.; Oumouch, S.; Guillemont, J.; Coupa, S.; Poncelet, A.; Csoka, I.; Meyer, C.; Andries, K.; Nguyen, C. H.; Grierson D. S.; Arnold E. J. *Med. Chem.* 2005, 48, 7582-91.
23) Tsuzuki, S.; Houjou, H.; Nagawa, Y.; Hiratani, K. J. *Chem. Soc. Perkin Trans.* 2 2002, 1271-1273.
24) Jorgensen, W. L.; Tirado-Rives, J. J. *Comput. Chem.* 2005, 26, 1689-1700.
25) Alanine, A.; Anselm, L.; Steward, L.; Thomi, S.; Vifian, W.; Groaning, M. D. *Bioorg. Med. Chem. Lett.* 2004, 14, 817-821.
26) Van Dort, M.; Neubig, R.; Counsell, R. E. *J. Med. Chem.* 1987, 30, 1241-1244.
27) Zinner, G.; Heitmann, M. *Arch. Pharm.* 1981, 314, 193-196.
28) Barreca, M. L.; De Luca, L.; Iraci, N.; Rao, A.; Ferro, S.; Maga, G.; Chimirri, A. J. *Chem. Inf. Model.* 2007, 47, 557-562.

The invention claimed is:
1. A compound according to the chemical structure:

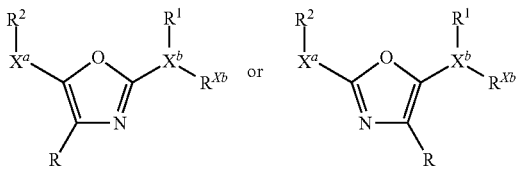

Where $X^a$ is N—$R^{NXa}$, $CR^{ba}R^{ba}$ or O;
$X^b$ is N or O;
$R^{Xb}$ is absent, H or an optionally substituted $C_1$-$C_3$ alkyl group;
$R^{NXa}$ is H or an optionally substituted $C_1$-$C_3$ alkyl group;
Each $R^{ba}$ is independently H or a $C_1$-$C_3$ alkyl group;
R is H, CN or a $C_1$-$C_3$ alkyl group;
$R^1$ is an optionally substituted aryl group; and
$R^2$ is an optionally substituted aryl group, or
a pharmaceutically acceptable salt, enantiomer or steroisomer thereof.
2. The compound according to claim 1 wherein R is H or CN.
3. The compound according to claim 1 wherein R is H.
4. The compound according to claim 2 wherein $X^a$ is $CR^{ba}R^{ba}$.
5. The compound according to claim 3 wherein $X^a$ is $CR^{ba}R^{ba}$.
6. The compound according to claim 4 wherein $R^{ba}$ is H or $CH_3$.
7. The compound according to claim 4 wherein each $R^{ba}$ is H.
8. The compound according to claim 3 wherein each $R^{ba}$ is H.
9. The compound according to claim 5 wherein each $R^{ba}$ is H.
10. The compound according to claim 1 wherein $X^b$ is N.
11. The compound according to claim 2 wherein $X^b$ is N.
12. The compound according to claim 7 wherein $X^b$ is N.
13. The compound according to claim 1 wherein $R^{Xb}$ is H or $CH_3$.
14. The compound according to claim 3 wherein $R^{Xb}$ is H or $CH_3$.
15. The compound according to claim 10 wherein $R^{Xb}$ is H or $CH_3$.
16. The compound according to claim 11 wherein $R^{Xb}$ is H or $CH_3$.
17. The compound according to claim 12 wherein $R^{Xb}$ is H or $CH_3$.
18. The compound according to claim 1 wherein $R^1$ and $R^2$ are each phenyl groups which are optionally substituted with 1, 2 or 3 substituents selected from the group consisting of F, Cl, Br, CN, $NO_2$ and $C_1$-$C_3$ alkyl.
19. The compound according to claim 2 wherein $R^1$ and $R^2$ are each phenyl groups each of which is optionally substituted with 1, 2 or 3 substituents selected from the group consisting of F, Cl, Br, CN, $NO_2$ and $C_1$-$C_3$ alkyl.
20. The compound according to claim 3 wherein $R^1$ and $R^2$ are each phenyl groups each of which is optionally substituted with 1, 2 or 3 substituents selected from the group consisting of F, Cl, Br, CN, $NO_2$ and $C_1$-$C_3$ alkyl.
21. The compound according to claim 8 wherein $R^1$ and $R^2$ are each phenyl groups each of which is optionally substituted with 1, 2 or 3 substituents selected from the group consisting of F, Cl, Br, CN, $NO_2$ and $C_1$-$C_3$ alkyl.
22. The compound according to claim 9 wherein $R^1$ and $R^2$ are each phenyl groups each of which is optionally substituted with 1, 2 or 3 substituents selected from the group consisting of F, Cl, Br, CN, $NO_2$ and $C_1$-$C_3$ alkyl.
23. The compound according to claim 15 wherein $R_1$ and $R^2$ are each phenyl groups each of which is optionally substituted with 1, 2 or 3 substituents selected from the group consisting of F, Cl, Br, CN, $NO_2$ and $C_1$-$C_3$ alkyl.
24. The compound according to claim 16 wherein $R^1$ and $R^2$ are each phenyl groups each of which is optionally substituted with 1, 2 or 3 substituents selected from the group consisting of F, Cl, Br, CN, $NO_2$ and $C_1$-$C_3$ alkyl.
25. The compound according to claim 17 wherein $R^1$ and $R^2$ are each phenyl groups each of which is optionally substituted with 1, 2 or 3 substituents selected from the group consisting of F, Cl, Br, CN, $NO_2$ and $C_1$-$C_3$ alkyl.
26. The compound according to claim 18 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.
27. The compound according to claim 19 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.
28. The compound according to claim 20 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.
29. The compound according to claim 21 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.

30. The compound according to claim 22 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.

31. The compound according to claim 23 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.

32. The compound according to claim 24 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.

33. The compound according to claim 25 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.

34. The compound according to claim 26 wherein $R^1$ is substituted with 1 or 2 substituents selected from the group consisting of F, Cl, CN and $C_1$-$C_3$ alkyl and $R^2$ is substituted with 3 substituents selected from the group consisting of F, Cl, CN and $C_1$-$C_3$ alkyl.

35. The compound according to claim 33 wherein $R^1$ has 2 substituents selected from the group consisting of F, Cl and CN and $R^2$ has three substituents selected from the group consisting of F, Cl, and $C_1$-$C_3$ alkyl.

36. The compound according to claim 34 wherein $R^1$ has 2 substituents selected from the group consisting of F, Cl and CN and $R^2$ has three substituents selected from the group consisting of F, Cl, and $C_1$-$C_3$ alkyl.

37. The compound according to claim 33 wherein $R^1$ has one substituent which is CN and $R^2$ has three substituents selected from group consisting of F and $C_1$-$C_3$ alkyl.

38. The compound according to claim 34 wherein $R^1$ has one substituent which is CN and $R^2$ has three substituents selected from the group consisting of F and $C_1$-$C_3$ alkyl.

39. The compound according to claim 35 wherein said $R^1$ substituents are Cl and CN and said $R^2$ substituents are F and $C_1$-$C_3$ alkyl.

40. The compound according to claim 36 wherein said $R^1$ substituents are Cl and CN and said $R^2$ substituents are F and $C_1$-$C_3$ alkyl.

41. The compound according to claim 37 wherein said $C_1$-$C_3$ alkyl group is ethyl.

42. The compound according to claim 38 wherein said $C_1$-$C_3$ alkyl group is ethyl.

43. The compound according to claim 39 wherein said $C_1$-$C_3$ alkyl group is isopropyl.

44. The compound according to claim 40 wherein said $C_1$-$C_3$ alkyl group is ethyl.

45. The compound according to claim 1 wherein $X^a$ is $CR^{ba}R^{ba}$, $X^b$ is N, $R^{Xb}$ is H, each $R^{ba}$ is H, R is H, $R^1$ is a phenyl group substituted with 1 or 2 substituents selected from the group consisting of F, Cl, CN and $C_1$-$C_3$ alkyl and $R^2$ is phenyl group substituted with 3 substituents selected from the group consisting of F, Cl, CN and $C_1$-$C_3$ alkyl or a pharmaceutically acceptable salt thereof.

46. The compound according to claim 45 wherein $R^1$ has one substituent which is CN and $R^2$ has three substituents selected from group consisting of F and $C_1$-$C_3$ alkyl.

47. The compound according to claim 45 wherein $R^1$ has 2 substituents selected from the group consisting of F, Cl and CN and $R^2$ has three substituents selected from the group consisting of F, Cl, and $C_1$-$C_3$ alkyl.

48. The compound according to claim 46 wherein said $C_1$-$C_3$ alkyl is ethyl.

49. The compound according to claim 47 wherein said $R^1$ substituents are Cl and CN and said $R^2$ substituents are selected from the group consisting of F and $C_1$-$C_3$ alkyl.

50. The compound according to claim 49 wherein said $C_1$-$C_3$ alkyl is isopropyl.

51. A pharmaceutical composition comprising an effective amount of a compound according to claim 1 in combination with a pharmaceutically acceptable carrier, additive or excipient.

52. A pharmaceutical composition comprising an effective amount of a compound according to claim 2 in combination with a pharmaceutically acceptable carrier, additive or excipient.

53. A pharmaceutical composition comprising an effective amount of a compound according to claim 45 in combination with a pharmaceutically acceptable carrier, additive or excipient.

54. A pharmaceutical composition comprising an effective amount of a compound according to claim 48 in combination with a pharmaceutically acceptable carrier, additive or excipient.

55. A pharmaceutical composition comprising an effective amount of a compound according to claim 49 in combination with a pharmaceutically acceptable carrier, additive or excipient.

56. A pharmaceutical composition comprising an effective amount of a compound according to claim 50 in combination with a pharmaceutically acceptable carrier, additive or excipient.

57. The pharmaceutical composition according to claim 51 further comprising an effective amount of another anti-HIV agent.

58. The pharmaceutical composition according to claim 53 further comprising an effective amount of another anti-HIV agent.

59. The pharmaceutical composition according to claim 57 wherein said anti-HIV agents is selected from the group consisting of nucleoside reverse transcriptase inhibitors (NRTI), other non-nucleoside reverse transcriptase inhibitors (NNRTI), fusion inhibitors and mixtures thereof.

60. The pharmaceutical composition according to claim 58 wherein said anti-HIV agents is selected from the group consisting of nucleoside reverse transcriptase inhibitors (NRTI), other non-nucleoside reverse transcriptase inhibitors (NNRTI), fusion inhibitors and mixtures thereof.

61. A method of treating an HIV infection in a patient in need comprising administering to said patient an effective amount of a compound according to claim 1 in combination with a pharmaceutically acceptable carrier, additive or excipient.

62. A method of treating an HIV infection in a patient in need comprising administering to said patient an effective amount of a compound according to claim 45 in combination with a pharmaceutically acceptable carrier, additive or excipient.

63. A method of reducing the likelihood of an HIV infection in a patient at risk for said infection comprising administering to said patient an effective amount of a compound according to claim 1 in combination with a pharmaceutically acceptable carrier, additive or excipient.

64. A method of reducing the likelihood of an HIV infection in a patient at risk for said infection comprising administering to said patient an effective amount of a compound according to claim 45 in combination with a pharmaceutically acceptable carrier, additive or excipient.

65. A method of treating AIDS or ARC in a patient in need comprising administering to said patient an effective amount of a compound according to claim 1 in combination with a pharmaceutically acceptable carrier, additive or excipient.

66. A method of treating AIDS or ARC in a patient in need comprising administering to said patient an effective amount of a compound according to claim 45 in combination with a pharmaceutically acceptable carrier, additive or excipient.

67. A method of inhibiting HIV reverse transcriptase in a subject, comprising administering to said subject an effective amount of a compound according to claim 1.

68. A method of inhibiting HIV reverse transcriptase in a subject, comprising administering to said subject an effective amount of a compound according to claim 45.

* * * * *